United States Patent
Pingali et al.

(10) Patent No.: US 9,273,041 B2
(45) Date of Patent: Mar. 1, 2016

(54) COMPOUNDS FOR THE TREATMENT OF DYSLIPIDEMIA AND RELATED DISEASES

(75) Inventors: Harikishore Pingali, Ahmedabad (IN); Pankaj Makadia, Ahmedabad (IN); Vrajesh Pandya, Ahmedabad (IN); Sairam V. V. M. Kalapatapu, Ahmedabad (IN)

(73) Assignee: Cadila Healthcare Limited (IN)

( * ) Notice: Subject to any disclaimer, the term of this patent is extended or adjusted under 35 U.S.C. 154(b) by 0 days.

(21) Appl. No.: 14/381,476

(22) PCT Filed: Jun. 26, 2012

(86) PCT No.: PCT/IN2012/000452
§ 371 (c)(1),
(2), (4) Date: Aug. 27, 2014

(87) PCT Pub. No.: WO2013/132509
PCT Pub. Date: Sep. 12, 2013

(65) Prior Publication Data
US 2015/0099696 A1    Apr. 9, 2015

(30) Foreign Application Priority Data
Mar. 7, 2012 (IN) .......................... 612/MUM/2012

(51) Int. Cl.
| | | |
|---|---|---|
| A61K 45/06 | (2006.01) |
| C07D 407/12 | (2006.01) |
| C07D 417/12 | (2006.01) |
| C07D 403/12 | (2006.01) |
| C07D 413/14 | (2006.01) |
| C07D 405/12 | (2006.01) |
| C07D 409/12 | (2006.01) |
| C07D 413/12 | (2006.01) |
| A61K 31/4155 | (2006.01) |
| A61K 31/422 | (2006.01) |
| A61K 31/427 | (2006.01) |
| A61K 31/4433 | (2006.01) |
| A61K 31/506 | (2006.01) |

(52) U.S. Cl.
CPC .......... *C07D 417/12* (2013.01); *A61K 31/4155* (2013.01); *A61K 31/422* (2013.01); *A61K 31/427* (2013.01); *A61K 31/4433* (2013.01); *A61K 31/506* (2013.01); *A61K 45/06* (2013.01); *C07D 403/12* (2013.01); *C07D 405/12* (2013.01); *C07D 409/12* (2013.01); *C07D 413/12* (2013.01); *C07D 413/14* (2013.01)

(58) Field of Classification Search
CPC .............................. C07D 407/12; A61K 45/06
See application file for complete search history.

(56) References Cited

FOREIGN PATENT DOCUMENTS

WO    WO-2011/051961 A1    5/2011
WO    WO-2013/132509 A1    9/2013

OTHER PUBLICATIONS

Ito, M. "Dyslipidemia: Management Using Optimal Lipid-Lowering Therapy." The Annals of Pharmacotherapy. (2012), vol. 46 (10), pp. 1368-1381.*
ClinicalKey. "Hyperlipidemia." © 2013. Available from: < https://www.clinicalkey.com/topics/cardiology/hyperlipidemia.html >.*
Utah Valley University. OChem Portal. "Alkenyl Group." (c) 2015. Available from: < http://science.uvu.edu/ochem/index.php/alpha-betical/a-b/alkenyl-group/ >.*
Utah Valley University. OChem Portal. "Alkynyl Group." © 2015. Available from: < http://science.uvu.edu/ochem/index.php/alpha-betical/a-b/alkynyl-group/printpage/ >.*
"International Application Serial No. PCT/IN2012/000452, International Preliminary Report on Patentability dated Sep. 9, 2014", 4 pgs.
"International Application Serial No. PCT/IN2012/000452, International Search Report mailed Feb. 1, 2013", 2 pgs.
"International Application Serial No. PCT/IN2012/000452, Written Opinion mailed Feb. 1, 2013", 3 pgs.
Abifadel, Marianne, et al., "Mutations in *PCSK9* cause autosomal dominant hypercholesterolemia.", *Nat. Genet.*, 34(2), (2003), 154-156.
Chan, Joyce C. Y., et al., "A proprotein convertase subtilisin/kexin type 9 neutralizing antibody reduces serum cholesterol in mice and nonhuman primates", *Proc. Natl. Acad. Sci. USA*, 106(24), (2009), 9820-9825.
Costet, Philippe, et al., "PCSK9 and LDL cholesterol: unravelling the target to design the bullet", *Trends in Biochemical Sciences*, 33(9), (2008), 426-434.
Cunningham, David, et al., "Structural and biophysical studies of PCSK9 and its mutants linked to familial hypercholesterolemia", *Nature Structural & Molecular Biology*, 14, (2007), 413-419.
Duff, Christopher J., et al., "Antibody-mediated disruption of the interaction between PCSK9 and the low-density lipoprotein receptor", *Biochemical Journal*, 419, (2009), 577-584.

(Continued)

*Primary Examiner* — Noble Jarrell
*Assistant Examiner* — John S Kenyon
(74) *Attorney, Agent, or Firm* — Schwegman Lundberg & Woessner, P.A.

(57) ABSTRACT

The present invention relates to compounds of the general formula (I), their tautomeric forms, their stereoisomers, their pharmaceutically acceptable salts, pharmaceutical compositions containing them, methods for their preparation, use of these compounds in medicine and the intermediates involved in their preparation. The present invention is directed to compounds suitable for the treatment of Disease conditions such as hyperlipidemia.

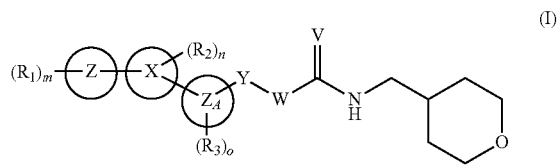

14 Claims, No Drawings

(56) References Cited

OTHER PUBLICATIONS

Frank-Kamenetsky, Maria, "Therapeutic RNAi targeting PCSK9 acutely lowers plasma cholesterol in rodents and LDL cholesterol in nonhuman primates", *Proc. Natl. Acad. Sci. USA*, 105(33), (2008), 11915-11920.

Graham, Mark J., et al., "Antisense inhibition of proprotein convertase subtilisin/kexin type 9 reduces serum LDL in hyperlipidemic mice", *Journal of Lipid Research*, 48(4), (2007), 763-767.

Lopez, D., "Inhibition of PCSK9 as a novel strategy for the treatment of hypercholesterolemia", (Abstract Only), *Drug News Perspect.*, 21(6), 323-330, (2008), 1 pg.

McNutt, Markey C., et al., "Antagonism of Secreted PCSK9 Increases Low Density Lipoprotein Receptor Expression in HepG2 Cells", *The Journal of Biological Chemistry*, 284(16), (2009), 10561-10570.

Montalbetti, Christian A. G. N., et al., "Amide bond formation and peptide coupling", *Tetrahedron*, 61, (2005), 10827-10852.

Pandit, Shilpa, et al., "Functional analysis of sites within PCSK9 responsible for hypercholesterolemia", *Journal of Lipid Research*, 49, (2008), 1333-1343.

Piper, D. E., et al., "The Crystal Structure of PCSK9: a Regulator of Plasma LDL-Cholesterol", *Structure*, 15(5), (2007), 545-552.

Steinberg, Daniel, et al., "Inhibition of PCSK9: A powerful weapon for achieving ideal LDL cholesterol levels", *Proc. Natl. Acad. Sci. USA*, 106(24), (2009), 9546-9547.

\* cited by examiner

COMPOUNDS FOR THE TREATMENT OF DYSLIPIDEMIA AND RELATED DISEASES

PRIORITY APPLICATIONS

This application is a U.S. National Stage Filing under 35 U.S.C. 371 from International Application No. PCT/IN2012/000452, filed on 26 Jun. 2012, and published as WO 2013/132509 A1 on 12 Sep. 2013, which claims the benefit to Indian Application No. 612/MUM/2012, filed on 7 Mar. 2012; which applications and publication are incorporated herein by reference in their entirety.

FIELD OF INVENTION

The present invention relates to compounds of the general formula (I), their tautomeric forms, their stereoisomers, their pharmaceutically acceptable salts, pharmaceutical compositions containing them, methods for their preparation, use of these compounds in medicine and the intermediates involved in their preparation The present invention is directed to compounds suitable for the treatment of Disease conditions such as hyperlipidemia. The compounds of the present invention also lower LDL-c.

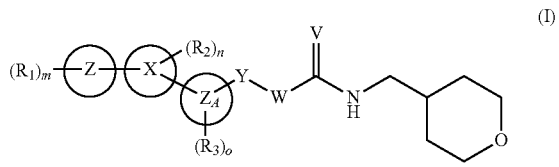

The compounds of the general formula (I) lower or modulate cholesterol levels and/or low-density lipoproteins (LDL) and/or triglyceride levels and raises the high-density lipoproteins (HDL) plasma levels and hence are useful in combating different medical conditions, where such lowering (and raising) is beneficial. Thus, it could be used in the treatment and/or prophylaxis of obesity, hyperlipidaemia; hypercholesteremia, hypertension, atherosclerotic disease events, vascular restenosis, diabetes and many other related conditions.

The compounds of general formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders.

These compounds of general formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis, diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

The compounds of the present invention can be useful as aldose reductase inhibitors; for improving cognitive functions in dementia, and in the treatment and/or prophylaxis of disorders such as psoriasis, polycystic ovarian syndrome (PCOS), cancer, osteoporosis, leptin resistance, inflammation and inflammatory bowel diseases, wound healing, xanthoma, pancreatitis, myotonic dystrophy, endothelial cell dysfunction and hyperlipidemia.

BACKGROUND OF THE INVENTION

Higher LDL cholesterol levels in the plasma increase cardiovascular risk and reduction in the levels of LDL would decrease CVD risk by a comparable percentage (PNAS, 2009, 106, 9546-9547). Clearance of LDL cholesterol from plasma is through the action of LDL receptors in the liver and LDL receptors are cell surface glycoproteins that bind to apoliporpotein B100 (apoB100) on LDL particles with high affinity and mediate their endocytic uptake (Journal of Biological Chemistry, 2009, 284, 10561-10570). Defect in hepatic cholesterol clearance and elevated levels of plasma LDL cholesterol that result from the mutations cause familial hypercholesterolemia. Such mutations are identified in the human LDL receptor and later in apolipoprotein-B (Nature Structural and Molecular Biology, 2007, 14, 413-419). Recently, mutations within the pro-protein convertase subtilisin/kexin of the subtype 9 (PCSK 9) gene were found to represent a third class of mutations associated with autosomal dominant hypercholesterolemia (ADH). Abifadel et al in 2003 discovered pro-protein convertase subtilisin/kexin of the subtype 9 as the third gene involved in autosomal dominant hypercholesterolaemia (ADH) (Nature Genetics, 2003, 34, 154-156, Trends in Biochemical Sciences, 2008, 33, 426-434). Several mis sense mutations (S127R, D129G, F216L, D374H, D374Y) are associated with hyperdiolesterolemia and premature atherosclerosis (J Lipid Res. 2008, 49, 1333-1343). Loss-of-function mutations (R46L, L253F, A433T) lead to elevated receptor abundance, enhancing clearance of LDL cholesterol from the circulation and reducing cardiovascular risk (Nature Structural and Molecular Biology, 2007, 14, 413-419).

Pro-protein convertase subtilisin/kexin of the subtype 9 belongs to the subtilisin family of serine proteases and its protein structure consists of a pro-domain, catalytic domain, and cysteine/histidine rich C-terminal domain (Structure, 2007, 15, 545-552). Unlike other pro-protein convertases, wherein the pro-domain is further proteolytically processed to activate the serine protease, the pro-domain of secreted subtype remains intact and tightly bound. Within endoplasmic reticulum this enzyme undergoes autocatalytic process which results in release of ~14 kDa prodomain that remains associated with the catalytic/C-terminal domains, wherein the pro-domain serves as both a folding chaperon and as an inhibitor of enzymatic activity (Journal of Biological Chemistry, 2009, 284, 10561-10570).

It is well documented that epidermal growth factor-like repeat A (EGF-A) of LDLR interacts with this pro-protein subtype mainly with residues 367-381. This EGF-A interaction site is located >20 Å from the catalytic site of this pro-protein subtype. Once EGF-A and this pro-protein subtype interacts they form a complex with the LDLR that enters endosomal pathway and hence LDLR recycling is prevented leading to LDLR degradation. Detailed molecular mechanisms explaining the association of LDLR and this pro-protein subtype and LDLR degradation is not very clear (Drug News Perspectives, 2008, 21, 323-330). Because of inhibition of LDLR recycling, number of LDL receptors on the cell surface are decreased and this increases plasma LDL levels (PNAS, 2009, 106, 9546-9547).

Various approaches for inhibiting this pro-protein subtype are reported, including gene silencing by siRNA or antisense oligonucleotides, mAb disrupting protein-protein interactions or by peptides; all the above-mentioned strategies have shown lowering of LDL cholesterol which may be effective therapy for treating hypercholesterolemia (Biochemical Journal, 2009, 419, 577-584; PNAS, 2008, 105, 11915-11920; Journal of Lipid Research, 2007, 48, 763-767; PNAS, 2009, 106, 9820-9825). However, very little success has been reported in trying to inhibit this pro-protein subtype by using small molecules. Small molecule inhibitors of this pro-protein subtype has its obvious clinical and therapeutic benefit over the other approaches as discussed above for the inhibition of pro-protein convertase subtilisin/kexin of the subtype 9. Small molecule inhibitors of this subtype have been disclosed by us in our application nos. 3556/MUM/2010 & 2292/MUM/2009. We herein disclose novel small molecules which have shown to inhibit the pro-protein convertase subtilisin/kexin of the subtype 9 in in-vitro studies and therefore provides an alternate beneficial approach for treating patients in need of such therapy.

PREFERRED EMBODIMENTS OF THE INVENTION

The main objective of the present invention is to provide novel compounds represented by the general formula (I), their tautomeric forms, their stereoisomers, their pharmaceutically acceptable salts, and pharmaceutical compositions containing them or their mixtures thereof.

In an embodiment of the present invention is provided a process for the preparation of novel compounds represented by the general formula (I), their tautomeric forms, their stereoisomers, their pharmaceutically acceptable salts.

In a further embodiment of the present invention is provided pharmaceutical compositions containing compounds of the general formula (I), their tautomeric forms, their stereoisomers, their pharmaceutically acceptable salts, or their mixtures in combination with suitable carriers, solvents, diluents and other media normally employed in preparing such compositions.

In a still further embodiment of the present invention is provided process for treatment of diseases mediated by the pro-protein convertase subtilisin/kexin of the subtype 9 enzyme by providing therapeutically effective amount of the compounds of formula (I) or their pharmaceutically acceptable salts or their suitable pharmaceutical compositions.

The above and other embodiments are described hereinafter.

DETAILED DESCRIPTION OF THE INVENTION

Accordingly, the present invention relates to compounds of the general formula (I),

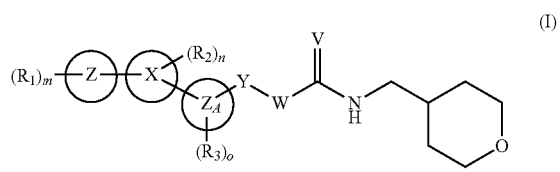

their tautomeric forms, their stereoisomers, their pharmaceutically acceptable salts, and pharmaceutical compositions containing them wherein '$Z_A$' represents an optionally substituted single or fused group selected from aryl, heterocyclyl or cycloalkyl groups;

Each of 'X' and 'Z' independently represents an optionally substituted single or fused group selected from aryl, heterocyclyl or cycloalkyl groups;

In a preferred embodiment, 'X' is selected from optionally substituted aryl or heterocyclyl groups;

In a further preferred embodiment, the aryl group may be selected from substituted or unsubstituted monocyclic or bicyclic aromatic groups;

In a still further preferred embodiment, the aryl group is an optionally substituted phenyl group.

In an embodiment, when 'X' represents a heterocyclyl group, the heterocyclyl group may be selected from single or fused mono, bi or tricyclic aromatic or non-aromatic groups containing one or more hetero atoms selected from O, N or S;

In a preferred embodiment, the heterocyclyl group may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl and the like;

In a preferred embodiment, either or both of 'Z' and '$Z_A$' is independently selected from optionally substituted aryl or heterocyclyl groups;

In a further preferred embodiment, when either of 'Z' and '$Z_A$' independently represents an aryl group, the aryl group may be selected from substituted or unsubstituted monocyclic or bicyclic aromatic groups;

In a still further preferred embodiment, such aryl group is an optionally substituted phenyl group.

In another embodiment, when either of 'Z' and '$Z_A$' independently represents a heterocyclyl group, the heterocyclyl group may be selected from single or fused mono or bi cyclic aromatic or non-aromatic groups containing one or more hetero atoms selected from O, N or S;

In a still preferred embodiment, when either of 'Z' and '$Z_A$' independently represents heteroaromatic group, the heteroaromatic group may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl groups.

Alternatively Z—X—$Z_A$ may together form tricyclic 8-15 membered fused ring system containing 1-4 hetero atoms selected from N, O or S.

$R_1$, $R_2$ and $R_3$ independently at each occurrence represents H, ($C_1$-$C_6$) linear or branched alkyl, ($C_1$-$C_6$) linear or branched alkenyl, ($C_1$-$C_6$) linear or branched alkynyl, hydroxy, ($C_1$-$C_6$) alkoxy, ($C_1$-$C_6$) alkenoxy, hydroxy($C_1$-$C_6$) alkyl, alkoxyalkyl, haloalkyl, ($C_3$-$C_6$) cycloalkyl, thio($C_1$-$C_6$)alkyl, ($C_1$-$C_6$)alkylthio, halo, oxo, imino, nitro, aryl, heterocyclyl, optionally substituted amino, amino($C_1$-$C_6$)alkyl, alkylamino, cyano, formyl, haloalkoxy, aryl, aryloxy, aralkyl, aralkoxy, heterocylyl, heterocyclylalkyl, heterocycloxy, heterocyclylalkoxy groups or the groups selected from carboxylic acid and its derivatives such as esters and amides, alkylsulfonyl, alkylsulfonylamino, alkylsulfonyloxy, each of which may be optionally substituted;

'm' 'n' and 'o' independently represents integers from 0 to 5;

'Y' represents either a bond, or O, S(O)$_p$ or —$NR_4$ wherein $R_4$ represents H, ($C_1$-$C_6$) linear or branched alkyl, ($C_3$-$C_6$) cycloalkyl, aryl, heterocyclyl, heterocyclylalkyl, cycloalkylalkyl and 'p' represents integers from 0 to 2;

'W' represents ($C_1$-$C_6$) linear or branched alkyl or ($C_3$-$C_6$) linear or branched cycloalkyl;

'V' represents O or S;

When any of $R_1$, $R_2$ or $R_3$ are substituted, such substituents may be selected from hydrogen, hydroxyl, oxo, halo, thiol, nitro, amino, cyano, formyl, or substituted or unsubstituted groups selected from amidino, alkyl, haloalkyl, perhaloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heterocyclylalkyl, heterocycloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, cycloalkylthio, arylthio, heterocyclylthio, alkylsulfinyl, cycloalkylsulfinyl, arylsulfinyl, heterocyclylsulfinyl, alkylsulfonyl, cycloalkylsulfonyl, arylsulfonyl, heterocyclylsulfonyl, alkylsulfonylamino, cycloalkylsulfonylamino, arylsulfonylamino, heterocyclylsulfonylamino, alkylsulfonyloxy, cycloalkylsulfonyloxy, arylsulfonyloxy, heterocyclylsulfonyloxy, alkoxycarbonylamino, aryloxycarbonylamino, aralkyloxycarbonylamino, aminocarbonylamino, alkylaminocarbonylamino, alkoxyamino, hydroxylamino, sulfonic acid and its derivatives;

When the aryl group at any occurrence is further substituted, the substituents are selected from halo, thiol, nitro, amino, cyano, formyl, or substituted or unsubstituted groups selected from amidino, alkyl, haloalkyl, perhaloalkyl, alkoxy, haloalkoxy, perhaloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heterocyclylalkyl, heterocycloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, cycloalkylthio, arylthio, heterocyclylthio groups;

When the heteroaryl group at any occurrence is further substituted, the substituents are selected from halo, thiol, nitro, amino, cyano, formyl, or substituted or unsubstituted groups selected from alkyl, haloalkyl, alkoxy, haloalkoxy, alkenyl, alkynyl, cycloalkyl, cycloalkenyl, alkenoxy, cycloalkoxy, aryl, aryloxy, aralkyl, aralkoxy, heterocylyl, heterocyclylalkyl, heterocycloxy, heterocyclylalkoxy, acyl, acylamino, monosubstituted or disubstituted amino, arylamino, aralkylamino, carboxylic acid and its derivatives such as esters and amides;

When the heterocyclyl group at any occurrence is further substituted, the substituents are selected from halo, amino, cyano, formyl, or substituted or unsubstituted groups selected from amidino, alkyl, haloalkyl, perhaloalkyl, alkoxy, haloalkoxy, perhaloalkoxy, alkenyl, alkynyl, cycloalkyl, cycloalkenyl, alkoxy, alkenoxy, cycloalkoxy, aryl, aryloxy, aralkyl, aralkoxy, heterocylyl, heterocyclylalkyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, cycloalkylthio, arylthio, heterocyclylthio groups.

The various groups, radicals and substituents used anywhere in the specification are described in the following paragraphs.

In a further preferred embodiment the groups, radicals described above may be selected from:

the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like;

the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains;

the "alkynyl" group used either alone or in combination with other radicals, is selected from a linear or branched radical containing two to six carbon atoms, more preferably thynyl, 1-propynyl, 2-propynyl, 1-butynyl, 2-butynyl, 3-butynyl, 1-pentynyl, 2-pentynyl, 3-pentynyl, 4-pentynyl, 1-hexynyl, and the like. The term "alkynyl" includes di- and tri-ynes wherever applicable;

the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like; The terms "bicycloalkyl" means more than one cycloalkyl groups fused together;

the "cycloalkenyl" group used either alone or in combination with other radicals, are preferably selected from cyclopropenyl, 1-cyclobutenyl, 2-cylobutenyl, 1-cyclopentenyl, 2-cyclopentenyl, 3-cyclopentenyl, 1-cyclohexenyl, 2-cyclohexenyl, 3-cyclohexenyl and the like; The terms "bicycloalkenyl" means more than one cycloalkenyl groups fused together;

the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like;

the "cycloalkoxy" group used either alone or in combination with other radicals, is selected from a cyclic radical containing three to seven carbons, more preferably cyclopropyloxy, cyclobutylxoy, cyclopentyloxy, cyclohexyloxy and the like; The terms "bicycloalkyloxy" means more than one cycloalkyl groups fused together;

the "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like;

the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups;

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

the "perhaloalkoxy" group is selected from a suitable perhaloalkyl radical, as defined above, directly attached to an oxygen atom, more preferably groups selected from trifluoromethoxy, trifluoroethoxy, and the like;

the "aryl" or "aromatic" group used either alone or in combination with other radicals, is selected from a suitable aromatic system containing one, two or three rings wherein such rings may be attached together in a pendant manner or may be fused, more preferably the groups are selected from phenyl, naphthyl, tetrahydronaphthyl, indane, biphenyl, and the like;

the "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like;

the 'aralkyl' group is selected from suitable aryl group as defined above attached to an alkyl group as defined above, more preferably selected from benzyl, phenethyl, naphthylmethyl, and the like;

the "aralkoxy" group is selected from a suitable arylalkyl group, as defined above, attached to an oxygen atom, more preferably the groups are selected from benzyloxy, phenethyloxy, naphthylmethyloxy, phenylpropyloxy, and the like, which may be substituted;

the "heterocyclyl" or "heterocyclic" group used either alone or in combination with other radicals, is selected from suitable aromatic or non-aromatic radicals containing one or more hetero atoms selected from O, N or S. The non-aromatic radicals may be saturated, partially saturated or unsaturated mono, bi or tricyclic radicals, containing one or more heteroatoms selected from nitrogen, sulfur and oxygen, more preferably selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, dihydrothiophene, dihydropyran, dihydrofuran, dihydrothiazole, benzopyranyl, benzopyranonyl, benzodihydrofuranyl, benzodihydrothienyl, pyrazolopyrimidonyl, azaquinazolinoyl, thienopyrimidonyl, quinazolonyl, pyrimidonyl, benzoxazinyl, benzoxazinonyl, benzothiazinyl, benzothiazinonyl, thieno piperidinyl, and the like; the aromatic radicals, may be selected from suitable single or fused mono, bi or tricyclic aromatic heterocyclic radicals containing one or more hetero atoms selected from O, N or S, more preferably the groups are selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzofuranyl, benzothienyl, indolinyl, indolyl, azaindolyl, azaindolinyl, pyrazolopyrimidinyl, azaquinazolinyl, pyridofuranyl, pyridothienyl, thienopyrimidyl, quinolinyl, pyrimidinyl, pyrazolyl, quinazolinyl, pyridazinyl, triazinyl, benzimidazolyl, benzotriazolyl, phthalazynil, naphthylidinyl, purinyl, carbazolyl, phenothiazinyl, phenoxazinyl, benzoxazolyl, benzothiazolyl and the like;

the groups "heterocycloxy", "heterocylylalkoxy" are selected from suitable heterocyclyl, heterocylylalkyl groups respectively, as defined above, attached to an oxygen atom;

the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted;

the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like;

the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted;

the "mono-substituted amino" group used either alone or in combination with other radicals, represents an amino group substituted with one group selected from ($C_1$-$C_6$) alkyl, substituted alkyl, aryl, substituted aryl or arylalkyl groups as defined earlier, more preferably such groups are selected from methylamine, ethylamine, n-propylamine, n-butylamine, n-pentylamine and the like;

the 'disubstituted amino" group used either alone or in combination with other radicals, represents an amino group, substituted with two radicals that may be same or different selected from ($C_1$-$C_6$)alkyl, substituted alkyl, aryl, substituted aryl, or arylalkyl groups, as defined above, more preferably the groups are selected from dimethylamino, methylethylamino, diethylamino, phenylmethyl amino and the like;

the "arylamino" used either alone or in combination with other radicals, represents an aryl group, as defined above, linked through amino having a free valence bond from the nitrogen atom, more preferably the groups are selected from phenylamino, naphthylamino, N-methyl anilino and the like;

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl;

the "carboxylic acid" group, used alone or in combination with other radicals, denotes a —COOH group, and includes derivatives of carboxylic acid such as esters and amides;

the "ester" group used alone or in combination with other radicals, denotes —COO— group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted;

the "amide" group used alone or in combination with other radicals, represents an aminocarbonyl radical ($H_2N-C=O$), wherein the amino group is mono- or di-substituted or unsubstituted, more preferably the groups are selected from methyl amide, dimethyl amide, ethyl amide, diethyl amide, and the like;

the "aminocarbonyl" group used either alone or in combination with other radicals, may be selected from 'aminocarbonyl', 'aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote aminocarbonyl radicals substituted, respectively, with one aryl radical, or one alkyl and one aryl radical. The term "aminocarbonylalkyl" includes alkyl radicals substituted with aminocarbonyl radicals;

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like;

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino;

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like;

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, the "thioalkyl" group used either alone or in combination with other radicals, denotes an alkyl group, as defined above, attached to a group of formula —SR', where R' represents hydrogen, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "arylthio" group used either alone or in combination with other radicals, denotes a comprising an aryl group as defined above, linked through a divalent sulfur atom having a free valence bond from the sulfur atom, more preferably the groups may be selected from phenylthio, naphthylthio, tetrahydronaphthylthio, indanethio, biphenylthio, and the like;

the "heterocyclylthio" group used either alone or in combination with other radicals, denotes a comprising an heterocyclyl group as defined above, linked through a divalent sulfur atom having a free valence bond from the sulfur atom;

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like;

the "aminocarbonylamino", "alkylaminocarbonylamino", "dialkylaminocarbonylamino" groups used alone or in combination with other radicals, is a carbonylamino (—$CONH_2$) group, attached to amino($NH_2$), alkylamino group or dialkylamino group respectively, where alkyl group is as defined above;

the "amidino" group used either alone or in combination with other radicals, represents a —C(=NH)—$NH_2$ radical; the "alkylamidino" group represents an alkyl radical, as described above, attached to an amidino group;

the "alkoxyamino" group used either alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above;

the "sulfenyl" group or "sulfenyl derivatives" used alone or in combination with other radicals, represents a bivalent group, —SO— or $R_xSO$, where $R_x$ is an optionally substituted alkyl, aryl, heteroaryl, heterocyclyl, group selected from those described above;

the "sulfonyl" group or "sulfones derivatives" used either alone or in combination with other radicals, with other terms such as alkylsulfonyl, represents a divalent radical —$SO_2$—, or $R_xSO_2$—, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

Suitable groups and substituents on the groups may be selected from those described anywhere in the specification.

The term "substituted," as used herein, means that any one or more hydrogens on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. The term "patient" means all mammals including humans. Examples of patients include humans, cows, dogs, cats, goats, sheep, pigs, and rabbits. Preferably, the patient is a human.

The term 'optional' or 'optionally' means that the subsequent described event or circumstance may or may not occur, and the description includes instances where the event or circumstance occur and instances in which it does not. For example, 'optionally substituted alkyl' means either 'alkyl' or 'substituted alkyl'. Further an optionally substituted group includes the unsubstituted group also.

Unless otherwise stated in the specification, structures depicted herein are also meant to include compounds which differ only in the presence of one or more isotopically enriched atoms. For example, compounds having the present structures wherein hydrogen is replaced by deuterium or tritium, or wherein carbon atom is replaced by 13C- or 14C-enriched carbon, are within the scope of this invention. Particularly useful compounds may be selected from 2-(4-(4-methyl-5-phenylisoxazol-3-yl)phenoxy)-N-((tetrahydro-2H-pyran-4-yl)methyl)acetamide;

2-(4-(5-methyl-4-phenylisoxazol-3-yl)phenoxy)-N-((tetrahydro-2H-pyran-4-yl)methyl)acetamide;

2-(4-(5-(4-fluorophenyl)-4-methylisoxazol-3-yl)phenoxy)-N-((tetrahydro-2H-pyran-4-yl)methyl)acetamide;

2-(4-(5-(4-chlorophenyl)-4-methylisoxazol-3-yl)phenoxy)-N-((tetrahydro-2H-pyran-4-yl)methyl)acetamide;

2-(4-(4-methyl-5-(4-(trifluoromethyl)phenyl)isoxazol-3-yl)phenoxy)-N-((tetrahydro-2H-pyran-4-yl)methyl)acetamide;

2-(4-(4-methyl-5-(p-tolyl)isoxazol-3-yl)phenoxy)-N-((tetrahydro-2H-pyran-4-yl)methyl)acetamide;

2-(4-(4-methyl-5-phenylisothiazol-3-yl)phenoxy)-N-((tetrahydro-2H-pyran-4-yl)methyl)acetamide;

2-(4-(5-methoxy-1-(4-(trifluoromethyl)phenyl)-1H-pyrazol-3-yl)phenoxy)-N-((tetrahydro-2H-pyran-4-yl)methyl)acetamide;

2-(4-(1-(4-fluorophenyl)-5-methoxy-1H-pyrazol-3-yl)phenoxy)-N-((tetrahydro-2H-pyran-4-yl)methyl)acetamide;

2-(4-(5-methoxy-1-phenyl-1H-pyrazol-3-yl)phenoxy)-N-((tetrahydro-2H-pyran-4-yl)methyl)acetamide;

2-(4-(4-methyl-2-phenylthiazol-5-yl)phenoxy)-N-((tetrahydro-2H-pyran-4-yl)methyl)acetamide;

2-(4-(4-methyl-2-(4-(trifluoromethyl)phenyl)thiazol-5-yl)phenoxy)-N-((tetrahydro-2H-pyran-4-yl)methyl)acetamide;

2-(4-(2-(4-fluorophenyl)-4-methylthiazol-5-yl)phenoxy)-N-((tetrahydro-2H-pyran-4-yl)methyl)acetamide;

2-(4-(2-(4-bromophenyl)-4-methylthiazol-5-yl)phenoxy)-N-((tetrahydro-2H-pyran-4-yl)methyl)acetamide;

2-(4-(2-(4-chlorophenyl)-4-methylthiazol-5-yl)phenoxy)-N-((tetrahydro-2H-pyran-4-yl)methyl)acetamide;

2-(4-(4-methyl-2-(p-tolyl)thiazol-5-yl)phenoxy)-N-((tetrahydro-2H-pyran-4-yl)methyl)acetamide;

2-(4-(5-methyl-2-phenyloxazol-4-yl)phenoxy)-N-((tetrahydro-2H-pyran-4-yl)methyl)acetamide;

2-(4-(5-methyl-2-(4-(trifluoromethyl)phenyl)oxazol-4-yl)phenoxy)-N-((tetrahydro-2H-pyran-4-yl)methyl)acetamide;

2-(4-(2-(4-fluorophenyl)-5-methyloxazol-4-yl)phenoxy)-N-((tetrahydro-2H-pyran-4-yl)methyl)acetamide;

2-(4-(2-(4-bromophenyl)-5-methyloxazol-4-yl)phenoxy)-N-((tetrahydro-2H-pyran-4-yl)methyl)acetamide;

2-(4-(2-(4-chlorophenyl)-5-methyloxazol-4-yl)phenoxy)-N-((tetrahydro-2H-pyran-4-yl)methyl)acetamide;

2-(4-(5-methyl-2-(p-tolyl)oxazol-4-yl)phenoxy)-N-((tetrahydro-2H-pyran-4-yl)methyl)acetamide;

2-(4-(2-(4-methoxyphenyl)-5-methyloxazol-4-yl)phenoxy)-N-((tetrahydro-2H-pyran-4-yl)methyl)acetamide;

2-(4-(5-methyl-2-(pyridin-3-yl)oxazol-4-yl)phenoxy)-N-((tetrahydro-2H-pyran-4-yl)methyl)acetamide;

N-((tetrahydro-2H-pyran-4-yl)methyl)-2-(4-(5-(4-(trifluoromethyl)phenyl)-1,2,4-oxadiazol-3-yl)phenoxy)acetamide;

2-(4-(5 (4-fluorophenyl)-1,2,4-oxadiazol-3-yl)phenoxy)-N-((tetrahydro-2H-pyran-4-yl)methyl)acetamide;

2-(4-(5-(4-bromophenyl)-1,2,4-oxadiazol-3-yl)phenoxy)-N-((tetrahydro-2H-pyran-4-yl)methyl)acetamide;

2-(4-(5-(4-chlorophenyl)-1,2,4-oxadiazol-3-yl)phenoxy)-N-((tetrahydro-2H-pyran-4-yl)methyl)acetamide;

N-((tetrahydro-2H-pyran-4-yl)methyl)-2-(4-(5-(p-tolyl)-1,2,4-oxadiazol-3-yl)phenoxy)acetamide;

2-(4-(5-(4-fluorophenyl)-1,3,4-oxadiazol-2-yl)phenoxy)-N-((tetrahydro-2H-pyran-4-yl)methyl)acetamide;

N-((tetrahydro-2H-pyran-4-yl)methyl)-2-(4-(5-(4-(trifluoromethyl)phenyl)-1,3,4-oxadiazol-2-yl)phenoxy)acetamide;

2-(4-(5-(4-methoxyphenyl)-1,3,4-oxadiazol-2-yl)phenoxy)-N-((tetrahydro-2H-pyran-4-yl)methyl)acetamide;
2-(4-(5-(4-chlorophenyl)-1,3,4-oxadiazol-2-yl)phenoxy)-N-((tetrahydro-2H-pyran-4-yl)methyl)acetamide;
2-(4-(5-phenyl-1,3,4-oxadiazol-2-yl)phenoxy)-N-((tetrahydro-2H-pyran-4-yl)methyl)acetamide;
2-(4-(3-(4-fluorophenyl)-2-oxooxazolidin-5-yl)phenoxy)-N-((tetrahydro-2H-pyran-4-yl)methyl)acetamide;
2-(4-(3-(4-methoxyphenyl)-2-oxooxazolidin-5-yl)phenoxy)-N-((tetrahydro-2H-pyran-4-yl)methyl)acetamide;
2-(4-(4-phenyl-1H-1,2,3-triazol-1-yl)phenoxy)-N-((tetrahydro-2H-pyran-4-yl)methyl)acetamide;
2-(4-(5-methoxy-1-(4-(trifluoromethyl)benzyl)-1H-pyrazol-3-yl)phenoxy)-N-((tetrahydro-2H-pyran-4-yl)methyl)acetamide;
2-(4-(4,5-dimethyloxazol-2-yl)phenoxy)-N-((tetrahydro-2H-pyran-4-yl)methyl)acetamide;
2-(4-(5-(4-bromophenyl)-4-methylisoxazol-3-yl)phenoxy)-N-((tetrahydro-2H-pyran-4-yl)methyl)acetamide;
2-(4-(5-(4-methoxyphenyl)-4-methyl isoxazol-3-yl)phenoxy)-N-((tetrahydro-2H-pyran-4-yl)methyl)acetamide;
2-(4-(4-methyl-5-(4-(trifluoromethoxy)phenyl)isoxazol-3-yl)phenoxy)-N-((tetrahydro-2H-pyran-4-yl)methyl)acetamide;
2-(4-(5-(4-fluorophenyl)-4-methylisothiazol-3-yl)phenoxy)-N-((tetrahydro-2H-pyran-4-yl)methyl)acetamide;
2-(4-(5-(4-chlorophenyl)-4-methylisothiazol-3-yl)phenoxy)-N-((tetrahydro-2H-pyran-4-yl)methyl)acetamide;
2-(4-(5-(4-bromophenyl)-4-methylisothiazol-3-yl)phenoxy)-N-((tetrahydro-2H-pyran-4-yl)methyl)acetamide;
2-(4-(4-methyl-5-(p-tolyl)isothiazol-3-yl)phenoxy)-N-((tetrahydro-2H-pyran-4-yl)methyl)acetamide;
2-(4-(4-methyl-5-(4-(trifluoromethyl)phenyl)isothiazol-3-yl)phenoxy)-N-((tetrahydro-2H-pyran-4-yl)methyl)acetamide;
2-(4-(5-(4-methoxyphenyl)-4-methylisothiazol-3-yl)phenoxy)-N-((tetrahydro-2H-pyran-4-yl)methyl)acetamide;
2-(4-(4-methyl-5-(4-(trifluoromethoxy)phenyl)isothiazol-3-yl)phenoxy)-N-((tetrahydro-2H-pyran-4-yl)methyl)acetamide;
2-(4-(1-(4-chlorophenyl)-5-methoxy-1H-pyrazol-3-yl)phenoxy)-N-((tetrahydro-2H-pyran-4-yl)methyl)acetamide;
2-(4-(5-methoxy-1-(4-methoxyphenyl)-1H-pyrazol-3-yl)phenoxy)-N-((tetrahydro-2H-pyran-4-yl)methyl)acetamide;
2-(4-(5-methoxy-1-(4-(trifluoromethoxy)phenyl)-1H-pyrazol-3-yl)phenoxy)-N-((tetrahydro-2H-pyran-4-yl)methyl)acetamide;
2-(4-(1-(4-bromophenyl)-5-methoxy-1H-pyrazol-3-yl)phenoxy)-N-((tetrahydro-2H-pyran-4-yl)methyl)acetamide;
2-(4-(5-methoxy-1-(p-tolyl)-1H-pyrazol-3-yl)phenoxy)-N-((tetrahydro-2H-pyran-4-yl)methyl)acetamide;
2-(4-(3-(4-chlorophenyl)-2-oxooxazolidin-5-yl)phenoxy)-N-((tetrahydro-2H-pyran-4-yl)methyl)acetamide;
2-(4-(2-oxo-3-(4-(trifluoromethyl)phenyl)oxazolidin-5-yl)phenoxy)-N-((tetrahydro-2H-pyran-4-yl)methyl)acetamide;
2-(4-(2-oxo-3-(4-(trifluoromethoxy)phenyl)oxazolidin-5-yl)phenoxy)-N-((tetrahydro-2H-pyran-4-yl)methyl)acetamide;
2-(4-(3-(4-bromophenyl)-2-oxooxazolidin-5-yl)phenoxy)-N-((tetrahydro-2H-pyran-4-yl)methyl)acetamide;
2-(4-(2-oxo-3-(p-tolyl)oxazolidin-5-yl)phenoxy)-N-((tetrahydro-2H-pyran-4-yl)methyl)acetamide;
2-(4-(4-(4-chlorophenyl)-1H-1,2,3-triazol-1-yl)phenoxy)-N-((tetrahydro-2H-pyran-4-yl)methyl)acetamide;
N-((tetrahydro-2H-pyran-4-yl)methyl)-2-(4-(4-(4-(trifluoromethyl)phenyl)-1H-1,2,3-triazol-1-yl)phenoxy)acetamide;
N-((tetrahydro-2H-pyran-4-yl)methyl)-2-(4-(4-(4-(trifluoromethoxy)phenyl)-1H-1,2,3-triazol-1-yl)phenoxy)acetamide;
2-(4-(4-(4-bromophenyl)-1H-1,2,3-triazol-1-yl)phenoxy)-N-((tetrahydro-2H-pyran-4-yl)methyl)acetamide;
N-((tetrahydro-2H-pyran-4-yl)methyl)-2-(4-(4-(p-tolyl)-1H-1,2,3-triazol-1-yl)phenoxy)acetamide;
2-(4-(4-(4-fluorophenyl)-1H-1,2,3-triazol-1-yl)phenoxy)-N-((tetrahydro-2H-pyran-4-yl)methyl)acetamide;
2-(4-(4-(4-methoxyphenyl)-1H-1,2,3-triazol-1-yl)phenoxy)-N-((tetrahydro-2H-pyran-4-yl)methyl)acetamide.
{does it include the list of compounds at the end (with no data?)}
2-(4-(3-(4-chlorophenyl)-2-iminooxazolidin-5-yl)phenoxy)-N-((tetrahydro-2H-pyran-4-yl)methyl)acetamide;
2-(4-(6-(4-chlorophenyl)pyridin-2-yl)phenoxy)-N-((tetrahydro-2H-pyran-4-yl)methyl)acetamide
2-(4-(4-(4-chlorophenyl)pyrimidin-2-yl)phenoxy)-N-((tetrahydro-2H-pyran-4-yl)methyl)acetamide;
2-((8-(4-chlorophenyl)dibenzo[b,d]thiophen-3-yl)oxy)-N-((tetrahydro-2H-pyran-4-yl)methyl)acetamide;
2-(4-(7-chlorodibenzo[b,d]thiophen-2-yl)phenoxy)-N-((tetrahydro-2H-pyran-4-yl)methyl)acetamide.

The novel compounds of this invention may be prepared using the reactions and techniques as shown in scheme below and described in this section or elsewhere in the specification. The reactions are performed in solvents appropriate to the reagents and materials employed and are suitable for the transformations being affected. It is understood by those skilled in the art that the nature and order of the synthetic steps presented may be varied for the purpose of optimizing the formation of the compounds of the present invention. It will also be well appreciated that one or more of the reactants may be protected and deprotected for facile synthesis by techniques known to persons skilled in the art. It will also be appreciated that one or more of the compounds of the present invention may exist in stereoisomeric and/or diastereomeric forms. Such stereoisomers and/or diastereoisomers as well as their optical antipodes are to be construed to be within the scope of the present invention. It will also be well appreciated that one or more of these compounds may be converted to their salts and other derivatives based on the specific groups present on the compounds, which can be well comprehended by persons skilled in the art. Such salts and/or other derivatives, as the case may be should also be construed to be within the scope of the present invention.

Scheme: 1 The compounds of general formula (I) wherein all the symbols are as defined earlier, may be prepared by reactions outlined in Scheme 1 below which comprises:

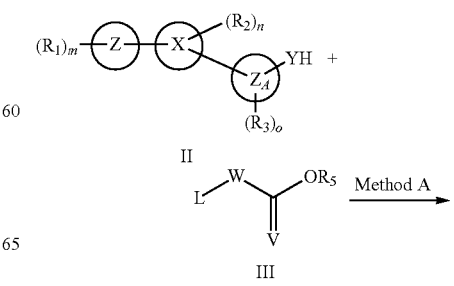

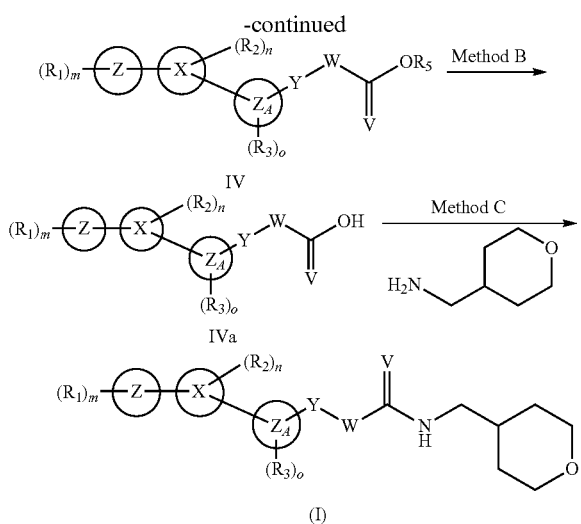

Method A:

The compounds of formula IV wherein $R_5$ represents $C_1$-$C_6$ linear or branched alkyl or aralkyl groups and all other symbols are as defined earlier may be prepared by the nucleophilic substitution reaction of compound of general formula II and compounds of general formula III wherein 'L' represents suitable leaving group and all other symbols are as defined earlier using suitable inorganic base(s) such as NaOH, KOH, $K_2CO_3$, $Cs_2CO_3$ and the like or organic base(s) such as pyridine, triethyl amine, diisopropyl ethylamine and the like. The reaction may be carried out neat or in presence of suitable protic solvent(s) such as methanol, ethanol, butanol and the like or suitable aprotic solvent(s) such as dimethyl formamide, tetrahydrofuran, dichloromethane and the like or suitable mixtures thereof. The reaction may be carried out at a temperature in the range 0° C. to reflux temperature of the solvent(s) used and the reaction time may range from 1 to 48 hours.

Method B:

The compounds of formula IV wherein all the symbols are as defined earlier may be hydrolyzed to compound of formula V wherein all the symbols are as defined earlier using suitable base(s) e.g., NaOH, LiOH, KOH and the like. Reaction may be conducted in suitable solvents e.g., alcohols like methanol, ethanol and the like, THF, water or the mixtures thereof. The reaction may be carried out at a temperature in the range 20° C. to reflux temperature of the solvent(s) used and the reaction time may range from 1 to 24 hours.

Method C:

The compounds of formula (I) wherein all the symbols are as defined earlier may be prepared by coupling reaction of corresponding acids of general formula V wherein all the symbols are as defined earlier and (tetrahydro-2H-pyran-4-yl)methanamine as described in scheme 1 under suitable conditions such as those described in Tetrahedron, 2005, 61(46), 10827-10852 with suitable modifications and alterations as are well known to a skilled person. The reaction may be carried out in presence of reagents(s) such as N-(3-dimethylaminopropyl)-N'-ethylcarbodimide hydrochloride (EDCl) & 1-Hydroxybenzotriazole (HOBT), and the like. The reaction may be carried in suitable solvent(s) such as dimethyl formamide, tetrahydrofuran, dichloromethane and the like or mixtures thereof. The reaction may be carried out at a temperature in the range 0° C. to reflux temperature of the solvent(s) used and the reaction time may range from 1 to 48 hours.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention can be used either alone or in combination with one or more therapeutic agents selected from insulin, insulin derivatives and mimetics, insulin secretagogues, insulin sensitizers, biguanide agents, alpha-glucosidase inhibitors, insulinotropic sulfonylurea receptor ligands, meglitinides, GLP-1 (glucagon like peptide-1), GLP-1 analogs, DPPIV (dipeptidyl peptidase IV) inhibitors, GPR-119 activators, sodium-dependent glucose co-transporter (SGLT2) inhibitors, PPAR modulators, non-glitazone type PPAR.delta agonist, HMG-CoA reductase inhibitors, cholesterol-lowering drugs, rennin inhibitors, anti-thrombotic and anti-platelet agents and anti-obesity agents or pharmaceutically acceptable salts thereof.

The invention is explained in greater detail by the examples given below, which are provided by way of illustration only and therefore should not be construed to limit the scope of the invention.

$^1$H NMR spectral data given in the examples (vide infra) are recorded using a 400 MHz spectrometer (Bruker AVANCE-400) and reported in δ scale. Until and otherwise mentioned the solvent used for NMR is $CDCl_3$ using tetramethyl silane as the internal standard.

Example 1

2-(4-(4-Methyl-5-phenyl isoxazol-3-yl)phenoxy)-N-((tetrahydro-2H-pyran-4-yl)methyl)acetamide Step 1: ethyl 2-(4-(4-methyl-5-phenylisoxazol-3-yl)phenoxy)acetate To a solution of 4-(4-methyl-5-phenylisoxazol-3-yl)phenol (1.1 gm, 4.38 mmoles) in DMF (10 ml), $K_2CO_3$ (1.2 gm, 5.26 mmoles) was added followed by the addition of ethyl chloro acetate (0.64 gm, 5.26 mmoles) at room temperature and the reaction mixture was stirred at room temperature for 18 hours. The reaction mixture was poured into ice cold water, solid separated was filtered, washed with water and dried over $P_2O_5$ under vacuum to yield 1.4 μm of title product as off white solid.

$^1$H NMR: 1.31 (t, J=5.6 Hz, 3H), 2.31 (s, 3H), 4.27 (q, J=7.1 Hz, 2H), 4.68 (s, 2H), 7.01-7.05 (m, 2H), 7.42-7.53 (m, 3H), 7.61-7.65 (m, 2H), 7.73-7.76 (m, 2H).

Step 2: 2-(4-(4-methyl-5-phenylisoxazol-3-yl)phenoxy)acetic acid

To a solution of the product of step 1 (1.4 gm, 4.15 mmoles) in a mixture of methanol (10 ml), THF (30 ml) and $H_2O$ (10 ml), lithium hydroxide (0.35 gm, 8.30 mmoles) was added and the reaction mixture was stirred at ambient temperature for 4 hours. The solvents were evaporated under reduced pressure. The residue was dissolved in water and acidified with 1N HCl. The solid separated which was filtered, washed with water & dried over P$_2$O$_5$ under vacuum to give 1.25 g of title product as pale brown solid.

$^1$H NMR: 2.31 (s, 3H), 4.75 (s, 2H), 7.05-7.07 (m, 2H), 7.45-7.53 (m, 3H), 7.65 (dd, J=7.0 & 2.2 Hz, 2H), 7.74-7.76 (m, 2H).

Step 3: 2-(4-(4-methyl-5-phenylisoxazol-3-yl)phenoxy)-N-((tetrahydro-2H-pyran-4-yl)methyl)acetamide To a solution of product of step 2 (309 mg, 1.00 mmoles) in DMF (3 mL), (tetrahydro-2H-pyran-4-yl)methanamine (126 mg, 1.10 mmoles), HOBT (202 mg, 1.50 mmoles), EDC.HCl (230 mg, 1.20 mmoles) and N-ethyl morpholine (345 mg, 3.00 mmoles) were added and reaction mixture was stirred at room temperature for 20 hours under nitrogen atmosphere. The reaction mixture was poured into ice cold water, solid separated was filtered, washed with water and dried over P$_2$O$_5$ under vacuum to yield 260 mg of title product as pale yellow solid.

$^1$H NMR: 1.28-1.39 (m, 2H), 1.61-1.62 (m, 2H), 1.76-1.85 (m, 1H), 2.31 (s, 3H), 3.26 (t, J=6.6 Hz, 2H), 3.33 (t, J=11.8 Hz, 2H), 3.95 (dd, J=11.0 & 3.4 Hz, 2H), 4.57 (s, 2H), 6.65 (bs, NH), 7.03-7.07 (m, 2H), 7.43-7.53 (m, 3H), 7.65-7.68 (m, 2H), 7.73-7.76 (m, 2H).

The following examples were prepared following the general procedures given in the Example 1 with suitable modifications, alterations and other process variations which are within the scope of a person skilled in the art.

Example 2

2-(4-(5-methyl-4-phenylisoxazol-3-yl)phenoxy)-N-((tetrahydro-2H-pyran-4-yl)methyl)acetamide $^1$HNMR (DMSO-d$_6$): 1.30-1.36 (m, 2H), 1.55-1.59 (m, 2H), 1.73-1.81 (m, 1H), 2.43 (s, 3H), 3.24 (t, J=6.6 Hz, 2H), 3.32 (t, J=11.8 Hz, 2H), 3.94 (dd, J=11.0 & 3.0 Hz, 2H), 4.48 (s, 2H), 6.83-6.87 (m, 2H), 7.15-7.18 (m, 2H), 7.33-7.42 (m, 5H).

Example 3

2-(4-(5-(4-fluorophenyl)-4-methylisoxazol-3-yl)phenoxy)-N-((tetrahydro-2H-pyran-4-yl)methyl)acetamide $^1$H NMR: 1.28-1.39 (m, 2H), 1.61-1.62 (m, 2H), 1.76-1.85 (m, 1H), 2.29 (s, 3H), 3.26 (t, J=6.6 Hz, 2H), 3.33 (t, J=11.0 Hz, 2H), 3.95 (dd, J=11.2 & 3.6 Hz, 2H), 4.57 (s, 2H), 6.65 (bs, NH), 7.03-7.07 (m, 2H), 7.18-7.24 (m, 2H), 7.63-7.67 (m, 2H), 7.72-7.76 (m, 2H).

Example 4

2-(4-(5-(4-chlorophenyl)-4-methylisoxazol-3-yl)phenoxy)-N-((tetrahydro-2H-pyran-4-yl)methyl)acetamide $^1$H NMR (DMSO-d$_6$): 1.07-1.18 (m, 2H), 1.48-1.51 (dd, J=1.6 & 12.8 Hz, 2H), 1.64-1.71 (m, 1H), 2.26 (s, 3H), 3.03 (t, J=6.4 Hz, 2H), 3.17-3.27 (m, 2H), 3.79-3.82 (dd, J=2.4 & 11.2 Hz, 2H), 4.58 (s, 2H), 7.12 (d, J=6.8 Hz, 2H), 7.62-7.68 (m, 4H), 7.80 (d, J=6.4 Hz, 2H), 8.17 (t, J=6.0 Hz, 1H).

Example 5

2-(4-(4-methyl-5-(4-(trifluoromethyl)phenyl)isoxazol-3-yl)phenoxy)-N-((tetrahydro-2H-pyran-4-yl)methyl)acetamide $^1$H NMR: 1.29-1.59 (m, 2H), 1.61-1.63 (m, 2H), 1.77-1.86 (m, 1H), 2.34 (s, 3H), 3.26 (t, J=6.6 Hz, 2H), 3.34 (t, J=11.8 Hz, 2H), 3.95 (dd, J=11.2 & 3.6 Hz, 2H), 4.57 (s, 2H), 6.65 (bs, NH), 7.05-7.08 (m, 2H), 7.64-7.68 (m, 2H), 7.77 (d, J=8.4 Hz, 2H), 7.87 (d, J=8.4 Hz, 21-1).

Example 6

2-(4-(4-methyl-5-(p-tolyl)isoxazol-3-yl)phenoxy)-N-((tetrahydro-2H-pyran-4-yl)methyl)acetamide $^1$H NMR: 1.25-1.38 (m, 2H), 1.58-1.62 (m, 2H), 1.76-1.85 (m, 1H), 2.29 (s, 3H), 2.43 (s, 3H), 3.3 (t, J=6.6 Hz, 2H), 3.33-3.39 (m, 2H), 3.95-3.99 (m, 2H), 4.57 (s, 2H), 6.66 (bs, NH), 7.03-7.06 (m, 2H), 7.31 (d, J=8.0 Hz, 2H), 7.63-7.68 (m, 4H).

Example 7

2-(4-(4-methyl-5-phenylisothiazol-3-yl)phenoxy)-N-((tetrahydro-2H-pyran-4-yl)methyl)acetamide $^1$H NMR (DMSO-d$_6$): 1.07-1.18 (m, 2H), 1.48-1.52 (m, 2H), 1.65-1.71 (m, 1H), 2.32 (s, 3H), 3.02 (t, J=6.4 Hz, 2H), 3.18-3.25 (m, 2H), 3.79-3.82 (m, 2H), 4.57 (s, 2H), 7.07-7.10 (m, 2H), 7.49-7.59 (m, 5H), 7.64-7.67 (m, 2H), 8.14 (t, J=6.0 Hz, 1H).

Example 8

2-(4-(5-methoxy-1-(4-(trifluoromethyl)phenyl)-1H-pyrazol-3-yl)phenoxy)-N-((tetrahydro-2H-pyran-4-yl)methyl)acetamide $^1$H NMR (DMSO-d$_6$): 1.08-1.18 (m, 2H), 1.49 (dd, J=12.8 & 1.6 Hz, 2H), 1.63-1.73 (m, 1H), 3.04 (t, J=6.4 Hz, 2H), 3.19-3.25 (m, 2H), 3.79-3.87 (m, 2H), 4.05 (s, 3H), 4.54 (s, 2H), 6.46 (s, 1H), 7.02-7.06 (m, 2H), 7.80-7.86 (m, 4H), 8.01 (d, J=8.4 Hz, 2H), 8.13 (t, J=5.8 Hz, 1H).

Example 9

2-(4-(1-(4-fluorophenyl)-5-methoxy-1H-pyrazol-3-yl)phenoxy)-N-((tetrahydro-2H-pyran-4-yl)methyl)acetamide $^1$H NMR (DMSO-d$_6$): 1.10-1.18 (m, 2H), 1.49 (dd, J=12.8 & 1.2 Hz, 2H), 1.65-1.71 (m, 1H), 3.03 (t, J=6.4 Hz, 2H), 3.19-3.25 (m, 2H), 3.79 (dd, J=11.2 & 2.0 Hz, 2H), 4.00 (s, 3H), 4.52 (s, 2H), 6.38 (s, 1H), 7.00-7.03 (m, 2H), 7.31-7.35 (m, 2H), 7.72-7.76 (m, 2H), 7.77-7.79 (m, 2H), 8.13 (t, J=6.0 Hz, 1H).

Example 10

2-(4-(5-methoxy-1-phenyl-1H-pyrazol-3-yl)phenoxy)-N-((tetrahydro-2H-pyran-4-yl)methyl)acetamide $^1$H NMR (DMSO-d$_6$): 1.10-1.15 (m, 2H), 1.49-1.52 (m, 2H), 1.65-1.71 (m, 1H), 3.03 (t, J=6.6 Hz, 2H), 3.19-3.25 (m, 2H), 3.83 (dd, J=11.2 & 2.4 Hz, 2H), 4.00 (s, 3H), 4.52 (s, 2H), 6.38 (s, 1H), 7.03 (d, J=9.2 Hz, 2H), 7.33 (d, J=8.0 Hz, 1H), 7.49 (t, J=7.8 Hz, 2H), 7.74 (dd J=8.4 & 1.2 Hz, 2H), 7.80 (d,d, J=6.8 &1.6 Hz, 2H), 8.13 (t, 1H).

Example 11

2-(4-(4-methyl-2-phenylthiazol-5-yl)phenoxy)-N-((tetrahydro-2H-pyran-4-yl)methyl)acetamide $^1$H NMR: 1.07-1.18 (m, 2H), 1.51 (d, J=12.8 Hz, 2H), 1.66-1.70 (m, 1H), 2.58 (s, 3H), 3.04 (t, J=6.6 Hz, 2H), 3.19-3.25 (m, 2H), 3.79-3.83 (dd, J=2.4 & 11.6 Hz, 2H), 4.55 (s, 2H), 7.07 (d, J=6.8 z, 2H), 7.46-7.52 (m, 3H), 7.68 (d, J=6.8 Hz, 2H), 7.91 (d, J=7.6 Hz, 2H), 8.15 (t. J=6.0 Hz, 1H).

Example 12

2-(4-(4-methyl-2-(4-(trifluoromethyl)phenyl)thiazol-5-yl)phenoxy)-N-((tetrahydro-2H-pyran-4-yl)methyl)acetamide 1H NMR: 1.28-1.39 (m, 2H), 1.59-1.62 (m, 2H), 1.79-1.83 (m, 1H), 2.62 (s, 3H), 3.28 (t, J=6.4 Hz, 2H), 3.34-3.40 (m, 2H), 3.96 (dd, J=11.2 & 3.2 Hz, 2H), 4.56 (s, 2H), 6.67 (s, NH), 7.01-7.04 (m, 2H), 7.67-7.72 (m, 4H), 8.04 (d, J=8.0 Hz, 2H).

Example 13

2-(4-(2-(4-fluorophenyl)-4-methylthiazol-5-yl)phenoxy)-N-((tetrahydro-2H-pyran-4-yl)methyl)acetamide 1H NMR: 1.25-1.39 (m, 2H), 1.58-1.62 (m, 2H), 1.78-1.84 (m, 1H), 2.58 (s, 3H), 3.27 (t, J=6.6 Hz, 2H), 3.33-3.40 (m, 2H), 3.95 (dd, J=10.4 & 4.0 Hz, 2H), 4.56 (s, 2H), 6.67 (bs, NH), 7.01 (d, J=6.8 z, 2H), 7.08-7.14 (m, 2H), 7.68 (d, J=6.8 Hz, 2H), 7.90-7.95 (m, 2H).

Example 14

2-(4-(2-(4-bromophenyl)-4-methylthiazol-5-yl)phenoxy)-N-((tetrahydro-2H-pyran-4-yl)methyl)acetamide 1H NMR (DMSO-$d_6$): 1.10-1.15 (m, 2H), 1.50 (d, J=13.2 Hz, 2H), 1.65-1.70 (m, 1H), 2.58 (s, 3H), 3.03 (t, J=6.4 Hz, 2H), 3.22 (t, J=11.6 Hz, 2H), 3.80 (dd, J=11.2 & 3.6 Hz, 2H), 4.55 (s, 2H), 7.06 (d, J=6.8 Hz, 2H), 7.67-7.71 (m, 4H), 7.86 (d, J=6.8 Hz, 2H), 8.15 (s, 1H).

Example 15

2-(4-(2-(4-chlorophenyl)-4-methylthiazol-5-yl)phenoxy)-N-((tetrahydro-2H-pyran-4-yl)methyl)acetamide 1H NMR (DMSO-$d_6$): 1.08-1.18 (m, 2H), 1.50 (d, J=9.8 Hz, 2H), 1.65-1.70 (m, 1H), 2.58 (s, 3H), 3.03 (t, J=6.4 Hz, 2H), 3.22 (t, J=10.0 Hz, 2H), 3.80 (dd, J=11.2 & 2.8 Hz, 2H), 4.55 (s, 2H), 7.07 (d, J=8.8 Hz, 2H), 7.57 (d, J=8.8 Hz, 2H), 7.68 (d, J=8.8 Hz, 2H), 7.94 (d, J=8.4 Hz, 2H), 8.17 (t, J=5.8 Hz, 1H).

Example 16

2-(4-(4-methyl-2-(p-tolyl)thiazol-5-yl)phenoxy)-N-((tetrahydro-2H-pyran-4-yl)methyl)acetamide 1H NMR (DMSO-$d_6$): 1.11-1.15 (m, 2H), 1.50 (d, J=11.2 Hz, 214), 1.65-1.71 (m, 1H), 2.35 (s, 3H), 2.56 (s, 3H), 3.04 (t, J=6.4 Hz, 2H), 3.22 (t, J=11.4 Hz, 2H), 3.80 (dd, J=11.6 & 3.2 Hz, 214), 4.55 (s, 2H), 7.06 (d, J=8.8 Hz, 2H), 7.30 (d, J=8.4 Hz, 2H), 7.67 (d, J=8.8 Hz, 2H), 7.80 (d, J=8.0 Hz, 2H), 8.15 (t, J=5.4 Hz, 1H).

Example 17

2-(4-(5-methyl-2-phenyloxazol-4-yl)phenoxy)-N-((tetrahydro-2H-pyran-4-yl)methyl)acetamide 1H NMR (DMSO-$d_6$): 1.10-1.18 (m, 2H), 1.48-1.52 (dd, J=1.6 & 12.8 Hz, 2H), 1.65-1.71 (m, 1H), 2.59 (s, 3H), 3.03 (t, J=6.4 Hz, 2H), 3.19-3.25 (m, 2H), 3.79-3.83 (dd, J=2.4 & 11.6 Hz, 2H), 4.53 (s, 2H), 7.05-7.08 (m, 2H), 7.49-7.56 (m, 3H), 7.65-7.69 (m, 2H), 7.97-8.00 (m, 2H), 8.14 (t, J=6.0 Hz, 1H).

Example 18

2-(4-(5-methyl-2-(4-(trifluoromethyl)phenyl)oxazol-4-yl)phenoxy)-N-((tetrahydro-2H-pyran-4-yl)methyl)acetamide $^1$H NMR (DMSO-$d_6$): 1.11-1.18 (m, 2H), 1.52 (d, J=13.2 Hz, 2H), 1.65-1.71 (m, 1H), 2.62 (s, 3H), 3.04 (t, J=6.4 Hz, 2H), 3.19-3.25 (m, 2H), 3.79-3.83 (dd, J=2.4 & 11.2 Hz, 2H), 4.54 (s, 2H), 7.07 (d, J=8.8 Hz, 2H), 7.69 (d, J=9.2 Hz, 2H), 7.91 (d, J=8.4 Hz, 2H), 8.13-8.20 (m, 2H).

Example 19

2-(4-(2-(4-fluorophenyl)-5-methyloxazol-4-yl)phenoxy)-N-((tetrahydro-2H-pyran-4-yl)methyl)acetamide 1H NMR (DMSO-$d_6$): 1.08-1.18 (m, 2H), 1.48-1.52 (m, 2H), 1.66-1.70 (m, 1H), 2.58 (s, 3H), 3.02 (t, J=6.6 Hz, 2H), 3.19-3.25 (m, 2H), 3.79-3.83 (M, 2H), 4.53 (s, 2H), 7.04-7.08 (m, 2H), 7.35-7.40 (m, 2H), 7.65-7.68 (m, 2H), 8.01-8.05 (m, 2H), 8.12 (t, J=6.0 Hz, 1H).

Example 20

2-(4-(2-(4-bromophenyl)-5-methyloxazol-4-yl)phenoxy)-N-((tetrahydro-2H-pyran-4-yl)methyl)acetamide 1H NMR (DMSO-$d_6$): 1.07-1.17 (m, 214), 1.50 (d, J=12.4 Hz, 2H), 1.65-1.71 (m, 1H), 2.59 (s, 3H), 3.03 (t, J=6.4 Hz, 2H), 3.22 (t, J=10.8 Hz, 2H), 3.81 (d, J=8.4 Hz, 2H), 4.53 (s, 2H), 7.06 (d, J=8.8 Hz, 2H), 7.67 (d, J=8.8 Hz, 2H), 7.74 (d, J=8.4 Hz, 2H), 7.92 (d, J=8.4 Hz, 2H), 8.15 (t, J=5.4 Hz, 1H).

Example 21

2-(4-(2-(4-chlorophenyl)-5-methyloxazol-4-yl)phenoxy)-N-((tetrahydro-2H-pyran-4-yl)methyl)acetamide 1H NMR (DMSO-d$_6$): 1.11-1.14 (m, 2H), 1.50 (d, J=12.8 Hz, 2H), 1.70 (m, 1H), 2.59 (s, 3H), 3.03 (t, J=6.4 Hz, 2H), 3.22 (t, J=11.6 Hz, 2H), 3.80 (dd, J=10.8 & 2.4 Hz, 2H), 4.53 (s, 2H), 7.06 (d, J=6.8 Hz, 2H), 7.60 (d, J=6.8 Hz, 2H), 7.66 (d, J=6.8 Hz, 2H), 7.98 (d, J=6.8 Hz, 2H), 8.14 (s, 1H).

Example 22

2-(4-(5-methyl-2-(p-tolyl)oxazol-4-yl)phenoxy)-N-((tetrahydro-2H-pyran-4-yl)methyl)acetamide 1H NMR (DMSO-d$_6$): 1.09-1.18 (m, 2H), 1.48-1.52 (m, 2H); 1.67-1.68 (m, 1H), 2.37 (s, 3H), 2.58 (s, 3H), 3.02 (t, J=6.4 Hz, 2H), 3.19-3.25 (m, 2H), 3.79-3.83 (m, 2H), 4.53 (s, 2H), 7.04-7.08 (m, 2H), 7.33 (d, J=8.0 Hz, 2H), 7.64-7.68 (m, 2H), 7.87 (d, J=8.0 Hz, 2H), 8.11 (t, J=6.0 Hz, 1H).

Example 23

2-(4-(2-(4-methoxyphenyl)-5-methyloxazol-4-yl)phenoxy)-N-((tetrahydro-2H-pyran-4-yl)methyl)acetamide 1H NMR (DMSO-d$_6$): 1.10-1.15 (m, 2H), 1.49-1.52 (m, 2H), 1.65-1.71 (m, 1H), 2.57 (s, 3H), 3.03 (t, J=6.6 Hz, 2H), 3.19-3.25 (m, 2H), 3.79-3.83 (m, 5H), 4.53 (s, 2H), 7.04-7.07 (m, 4H), 7.65 (d, J=7.2 Hz, 2H), 7.92 (d, J=7.2 Hz, 2H), 8.13 (s, NH).

Example 24

2-(4-(5-methyl-2-(pyridin-3-yl)oxazol-4-yl)phenoxy)-N-((tetrahydro-2H-pyran-4-yl)methyl)acetamide 1H NMR: 1.11-1.15 (m, 2H), 1.48-1.52 (m, 2H), 1.67-1.68 (m, 1H), 2.61 (s, 3H), 3.02 (t, J=6.4 Hz, 2H), 3.19-3.25 (m, 2H), 3.79-3.83 (m, 2H), 4.54 (s, 2H), 7.06 (dd, J=6.8 & 2.0 Hz, 2H), 7.56-7.59 (m, 1H), 7.67 (dd, J=7.2 & 2.0 Hz, 2H), 8.13-8.14 (m, 1H), 8.31-8.34 (m, 1H), 8.69-8.70 (m, 1H), 9.16 (d, J=1.6 Hz, 1H).

Example 25

N-((tetrahydro-2H-pyran-4-yl)methyl)-2-(4-(5-(4-(trifluoromethyl)phenyl)-1,2,4-oxadiazol-3-yl)phenoxy)acetamide 1H NMR (DMSO-d$_6$): 1.12-1.15 (m, 2H), 1.50-1.53 (m, 2H), 1.64-1.68 (m, 1H), 3.02 (t, J=6.4 Hz, 2H), 3.19-3.22 (m, 2H), 3.79-3.83 (m, 2H), 4.61 (s, 2H), 7.16 (d, J=8.0 Hz, 2H), 8.03-8.07 (m, 4H), 8.19 (t, J=6.0 Hz, 1H), 8.38 (d, J=8.0 Hz, 2H).

Example 26

2-(4-(5-(4-fluorophenyl)-1,2,4-oxadiazol-3-yl)phenoxy)-N-((tetrahydro-2H-pyran-4-yl)methyl)acetamide 1H NMR (DMSO-d$_6$): 1.11-1.15 (m, 2H), 1.49-1.52 (m, 2H), 1.68-1.69 (m, 1H), 3.02 (t, J=6.4 Hz, 2H), 3.19-3.22 (m, 2H), 3.79-3.83 (m, 2H), 4.60 (s, 2H), 7.15 (dd, J=6.8 & 2.0 Hz, 2H), 7.49-7.54 (m, 2H), 8.02 (dd, J=7.2 & 2.0 Hz, 2H), 8.19 (t, J=6.0 Hz, 1H), 8.23-8.27 (m, 2H).

Example 27

2-(4-(5-(4-bromophenyl)-1,2,4-oxadiazol-3-yl)phenoxy)-N-((tetrahydro-2H-pyran-4-yl)methyl)acetamide 1H NMR (DMSO-d$_6$): 1.08-1.18 (m, 2H), 1.51 (d, J=12.8 Hz, 2H), 1.65-1.71 (m, 1H), 3.03 (t, J=6.4 Hz, 2H), 3.22 (t, J=10.8 Hz, 2H), 3.80 (dd, J=11.2 & 2.4 Hz, 2H), 4.60 (s, 2H), 7.16 (d, J=8.8 Hz, 2H), 7.88 (d, J=8.4 Hz, 2H), 8.03 (d, J=8.8 Hz, 2H), 8.11 (d, J=8.4 Hz, 2H), 8.19 (t, J=6.0 Hz, 1H).

Example 28

2-(4-(5-(4-chlorophenyl)-1,2,4-oxadiazol-3-yl)phenoxy)-N-((tetrahydro-2H-pyran-4-yl)methyl)acetamide 1H NMR (DMSO-d$_6$): 1.08-1.18 (m, 2H), 1.51 (d, J=12.8 Hz, 2H), 1.65-1.70 (m, 1H), 3.04 (t, J=6.4 Hz, 2H), 3.22 (t, J=10.8 Hz, 2H), 3.80 (dd, J=11.2 & 2.8 Hz, 2H), 4.60 (s, 2H), 7.16 (d, J=8.8 Hz, 2H), 7.74 (d, J=8.8 Hz, 2H), 8.04 (d, J=8.8 Hz, 2H), 8.19 (d, J=8.4 Hz, 3H).

Example 29

N-((tetrahydro-2H-pyran-4-yl)methyl)-2-(4-(5-(p-tolyl)-1,2,4-oxadiazol-3-yl)phenoxy)acetamide 1H NMR (DMSO-d$_6$): 1.11-1.17 (m, 2H), 1.51 (d, J=13.2 Hz, 2H), 1.65-1.70 (m, 1H), 2.43 (s, 3H), 3.03 (t, J=6.4 Hz, 2H), 3.22 (t, J=11.6 Hz, 2H), 3.80 (dd, J=11.6 & 2.8 Hz, 2H), 4.60 (s, 2H), 7.15 (d, J=8.8 Hz, 2H), 7.47 (d, J=8.0 Hz, 2H), 8.03 (d, J=8.8 Hz, 2H), 8.07 (d, J=8.0 Hz, 2H), 8.18 (t, J=5.8 Hz, 1H).

Example 30

2-(4-(5-(4-fluorophenyl)-1,3,4-oxadiazol-2-yl)phenoxy)-N-((tetrahydro-2H-pyran-4-yl)methyl)acetamide 1H NMR (DMSO-d$_6$): 1.11-1.18 (m, 2H), 1.51 (d, J=12.8 Hz, 2H), 1.67-1.69 (m, 1H), 3.04 (t, J=6.4 Hz, 2H), 3.22 (t, J=11.6 Hz, 2H), 3.80 (dd, J=11.6 & 2.8 Hz, 2H), 4.62 (s, 2H), 7.18 (d, J=7.2 Hz, 2H), 7.48 (t, J=8.8 Hz, 2H), 8.08 (d, J=6.8 Hz, 2H), 8.17-8.21 (m, 3H).

Example 31

N-((tetrahydro-2H-pyran-4-yl)methyl)-2-(4-(5-(4-(trifluoromethyl)phenyl)-1,3,4-oxadiazol-2-yl)phenoxy)acetamide 1H NMR (DMSO-d$_6$): 1.08-1.18 (m, 2H), 1.51 (d, J=13.2 Hz, 2H), 1.66-1.71 (m, 1H), 3.04 (t, J=6.4 Hz, 2H), 3.23 (t, J=11.2 Hz, 2H), 3.81 (d, J=8.4 Hz, 2H), 4.63 (s, 2H), 7.20 (d, J=8.8 Hz, 2H), 8.01 (d, J=8.4 Hz, 2H), 8.11 (d, J=8.4 Hz, 2H), 8.20 (d, J=5.2 Hz, 1H), 8.34 (d, J=8.0 Hz, 2H).

Example 32

2-(4-(5-(4-methoxyphenyl)-1,3,4-oxadiazol-2-yl) phenoxy)-N-((tetrahydro-2H-pyran-4-yl)methyl) acetamide 1H NMR (DMSO-$d_6$): 1.08-1.18 (m, 2H), 1.50 (d, J=13.2 Hz, 2H), 1.65-1.71 (m, 1H), 3.04 (t, J=6.4 Hz, 2H), 3.20-3.26 (m, 2H), 3.80 (dd, J=11.6 & 2.8 Hz, 2H), 3.86 (s, 3H), 4.62 (s, 2H), 7.16-7.19 (m, 4H), 8.04 (dd, J=8.8 & 2 Hz, 4H), 8.19 (t, J=5.6 Hz, 1H),

Example 33

2-(4-(5-(4-chlorophenyl)-1,3,4-oxadiazol-2-yl)phenoxy)-N-((tetrahydro-2H-pyran-4-yl)methyl)acetamide $^1$H NMR (DMSO-$d_6$): 1.11-1.18 (m, 2H), 1.51 (d, J=12.8 Hz, 2H), 1.67-1.69 (m, 1H), 3.04 (t, J=6.2 Hz, 2H), 3.23 (t, J=11.2 Hz, 2H), 3.81 (d, J=8.8 Hz, 2H), 4.62 (s, 2H), 7.19 (d, J=8.4 Hz, 2H), 7.71 (d, J=8.4 Hz, 2H), 8.09 (d, J=8.8 Hz, 2H), 8.14 (d, J=8.4 Hz, 2H), 8.18 (d, J=5.2 Hz, 1H).

Example 34

2-(4-(5-phenyl-1,3,4-oxadiazol-2-yl)phenoxy)-N-((tetrahydro-2H-pyran-4-yl)methyl)acetamide 1H NMR (DMSO-$d_6$): 1.08-1.18 (m, 2H), 1.50 (t, J=13.2 Hz, 2H), 1.66-1.71 (m, 1H), 3.04 (t, J=6.4 Hz, 2H), 3.19-3.26 (m, 2H), 3.80 (dd, J=11.2 & 2.4 Hz, 2H), 4.63 (s, 2H), 7.17-7.20 (m, 2H), 7.60-7.66 (m, 3H), 8.07-8.08 (m, 2H), 8.09-8.14 (m, 2H), 8.20 (t, J=5.6 Hz, 1H).

Example 35

2-(4-(3-(4-fluorophenyl)-2-oxooxazolidin-5-yl)phenoxy)-N-((tetrahydro-2H-pyran-4-yl)methyl)acetamide 1H NMR: 1.08-1.16 (m, 2H), 1.46-1.49 (m, 2H), 1.65-1.66 (m, 1H), 2.99 (t, J=6.4 Hz, 2H), 3.18-3.21 (m, 2H), 3.78-3.82 (m, 2H), 3.98 (t, J=8.4 Hz, 1H), 4.38 (t, J=8.8 Hz, 1H), 4.51 (s, 2H), 5.66 (t, J=8.4 Hz, 1H), 7.01 (d, J=8.0 Hz, 2H), 7.22-7.27 (m, 2H), 7.45 (d, J=8.0 Hz, 2H), 7.60-7.63 (m, 2H), 8.01 (t, J=6 Hz, 1H).

Example 36

2-(4-(3-(4-methoxyphenyl)-2-oxooxazolidin-5-yl) phenoxy)-N-((tetrahydro-2H-pyran-4-yl)methyl) acetamide 1H NMR (DMSO-$d_6$): 1.05-1.62 (m, 2H), 1.46 (d, J=12.4 Hz, 2H), 1.63-1.68 (m, 1H), 3.01 (t, J=6.4 Hz, 2H), 3.18-3.24 (m, 2H), 3.74 (s, 3H), 3.78 (dd, J=11.2 & 2.4 Hz, 2H), 3.93-3.97 (m, 1H), 4.36 (t, J=9.0 Hz, 1H), 4.51 (s, 2H), 5.66 (t, J=8.4 Hz, 1H), 6.94-6.98 (m, 2H), 7.00-7.03 (m, 2H), 7.43 (dd, J=9.6 & 2.8 Hz, 2H), 7.47-7.51 (m, 2H), 8.11 (t, J=5.08 Hz, 1H).

Example 37

2-(4-(4-phenyl-1H-1,2,3-triazol-1-yl)phenoxy)-N-((tetrahydro-2H-pyran-4-yl)methyl)acetamide 1H NMR (DMSO-$d_6$): 1.14-1.18 (m, 2H), 1.48-1.52 (m, 2H), 1.65-1.70 (m, 1H), 3.02 (t, J=6.6 Hz, 2H), 3.19-3.24 (m, 2H), 3.79-3.82 (m, 2H), 4.59 (s, 2H), 7.16-7.20 (m, 2H), 7.35-7.39 (m, 1H), 7.47-7.50 (m, 2H), 7.84-7.88 (m, 2H), 7.91-7.94 (m, 2H), 8.16 (t, J=6.0 Hz, 1H), 9.18 (s, 1H).

Example 38

2-(4-(5-methoxy-1-(4-(trifluoromethyl)benzyl)-1H-pyrazol-3-yl)phenoxy)-N-((tetrahydro-2H-pyran-4-yl)methyl)acetamide 1H NMR (DMSO-$d_6$): 1.05-1.12 (m, 2H), 1.49 (d, J=12.8 Hz, 2H), 1.64-1.67 (m, 1H), 3.00 (t, J=6.4 Hz, 2H), 3.19 (t, J=10.4 Hz, 2H), 3.78 (s, 5H), 4.51 (s, 2H), 5.27 (s, 2H), 5.90 (s, 1H), 7.02 (d, J=8.8 Hz, 2H), 7.20 (d, J=8.0 Hz, 2H), 7.34 (d, J=8.8 Hz, 2H), 7.68 (d, J=8.0 Hz, 2H), 8.10 (t, J=5.8 Hz, 1H).

Example 39

2-(4-(4,5-dimethyloxazol-2-yl)phenoxy)-N-((tetrahydro-2H-pyran-4-yl)methyl)acetamide 1H NMR (DMSO-$d_6$): 1.10-1.17 (m, 2H), 1.47-1.51 (m, 2H), 1.64-1.70 (m, 1H), 2.06 (s, 3H), 2.29 (s, 3H), 3.02 (t, J=6.4 Hz, 2H), 3.21 (t, J=11.8 Hz, 2H), 3.78-3.82 (dd, J=11.2 & 2.4 Hz, 2H), 4.55 (s, 2H), 7.05 (d, J=6.8 Hz, 2H), 7.82 (d, J=6.8 Hz, 2H). The following compounds can be prepared by procedure similar to those described above with appropriate variations of reactions, reaction conditions and quantities of reagents.

Example 40

2-(4-(5-(4-bromophenyl)-4-methylisoxazol-3-yl) phenoxy)-N-((tetrahydro-2H-pyran-4-yl)methyl) acetamide

Example 41

2-(4-(5-(4-methoxyphenyl)-4-methylisoxazol-3-yl) phenoxy)-N-((tetrahydro-2H-pyran-4-yl)methyl) acetamide

Example 42

2-(4-(4-methyl-5-(4-(trifluoromethoxy)phenyl)isoxazol-3-yl)phenoxy)-N-((tetrahydro-2H-pyran-4-yl)methyl)acetamide

Example 43

2-(4-(5-(4-fluorophenyl)-4-methylisothiazol-3-yl)phenoxy)-N-((tetrahydro-2H-pyran-4-yl)methyl)acetamide

Example 44

2-(4-(5-(4-chlorophenyl)-4-methylisothiazol-3-yl)phenoxy)-N-((tetrahydro-2H-pyran-4-yl)methyl)acetamide

Example 45

2-(4-(5-(4-bromophenyl)-4-methylisothiazol-3-yl)phenoxy)-N-((tetrahydro-2H-pyran-4-yl)methyl)acetamide

Example 46

2-(4-(4-methyl-5-(p-tolyl)isothiazol-3-yl)phenoxy)-N-((tetrahydro-2H-pyran-4-yl)methyl)acetamide

Example 47

2-(4-(4-methyl-5-(4-(trifluoromethyl)phenyl)isothiazol-3-yl)phenoxy)-N-((tetrahydro-2H-pyran-4-yl)methyl)acetamide

Example 48

2-(4-(5-(4-methoxyphenyl)-4-methylisothiazol-3-yl)phenoxy)-N-((tetrahydro-2H-pyran-4-yl)methyl)acetamide

Example 49

2-(4-(4-methyl-5-(4-(trifluoromethoxy)phenyl)isothiazol-3-yl)phenoxy)-N-((tetrahydro-2H-pyran-4-yl)methyl)acetamide

Example 50

2-(4-(1-(4-chlorophenyl)-5-methoxy-1H-pyrazol-3-yl)phenoxy)-N-((tetrahydro-2H-pyran-4-yl)methyl)acetamide

Example 51

2-(4-(5-methoxy-1-(4-methoxyphenyl)-1H-pyrazol-3-yl)phenoxy)-N-((tetrahydro-2H-pyran-4-yl)methyl)acetamide

Example 52

2-(4-(5-methoxy-1-(4-(trifluoromethoxy)phenyl)-1H-pyrazol-3-yl)phenoxy)-N-((tetrahydro-2H-pyran-4-yl)methyl)acetamide

Example 53

2-(4-(1-(4-bromophenyl)-5-methoxy-1H-pyrazol-3-yl)phenoxy)-N-((tetrahydro-2H-pyran-4-yl)methyl)acetamide

Example 54

2-(4-(5-methoxy-1-(p-tolyl)-1H-pyrazol-3-yl)phenoxy)-N-((tetrahydro-2H-pyran-4-yl)methyl)acetamide

Example 55

2-(4-(3-(4-chlorophenyl)-2-oxooxazolidin-5-yl)phenoxy)-N-((tetrahydro-2H-pyran-4-yl)methyl)acetamide

Example 56

2-(4-(2-oxo-3-(4-(trifluoromethyl)phenyl)oxazolidin-5-yl)phenoxy)-N-((tetrahydro-2H-pyran-4-yl)methyl)acetamide

Example 57

2-(4-(2-oxo-3-(4-(trifluoromethoxy)phenyl)oxazolidin-5-yl)phenoxy)-N-((tetrahydro-2H-pyran-4-yl)methyl)acetamide

Example 58

2-(4-(3-(4-bromophenyl)-2-oxooxazolidin-5-yl)phenoxy)-N-((tetrahydro-2H-pyran-4-yl)methyl)acetamide

Example 59

2-(4-(2-oxo-3-(p-tolyl)oxazolidin-5-yl)phenoxy)-N-((tetrahydro-2H-pyran-4-yl)methyl)acetamide

Example 60

2-(4-(4-(4-chlorophenyl)-1H-1,2,3-triazol-1-yl)phenoxy)-N-((tetrahydro-2H-pyran-4-yl)methyl)acetamide

Example 61

N-((tetrahydro-2H-pyran-4-yl)methyl)-2-(4-(4-(4-(trifluoromethyl)phenyl)-1H-1,2,3-triazol-1-yl)phenoxy)acetamide

Example 62

N-((tetrahydro-2H-pyran-4-yl)methyl)-2-(4-(4-(4-(trifluoromethoxy)phenyl)-1H-1,2,3-triazol-1-yl)phenoxy)acetamide

Example 63

2-(4-(4-(4-bromophenyl)-1H-1,2,3-triazol-1-yl)phenoxy)-N-((tetrahydro-2H-pyran-4-yl)methyl)acetamide

Example 64

N-((tetrahydro-2H-pyran-4-yl)methyl)-2-(4-(4-(p-tolyl)-1H-1,2,3-triazol-1-yl)phenoxy)acetamide

Example 65

2-(4-(4-(4-fluorophenyl)-1H-1,2,3-triazol-1-yl)phenoxy)-N-((tetrahydro-2H-pyran-4-yl)methyl)acetamide

Example 66

2-(4-(4-(4-methoxyphenyl)-1H-1,2,3-triazol-1-yl)phenoxy)-N-((tetrahydro-2H-pyran-4-yl)methyl)acetamide

Example 67

2-(4-(3-(4-chlorophenyl)-2-iminooxazolidin-5-yl)phenoxy)-N-((tetrahydro-2H-pyran-4-yl)methyl)acetamide

Example 68

2-(4-(6-(4-chlorophenyl)pyridin-2-yl)phenoxy)-N-((tetrahydro-2H-pyran-4-yl)methyl)acetamide

Example 69

2-(4-(4-(4-chlorophenyl)pyrimidin-2-yl)phenoxy)-N-((tetrahydro-2H-pyran-4-yl)methyl)acetamide

Example 70

2-((8-(4-chlorophenyl)dibenzo[b,d]thiophen-3-yl)oxy)-N-((tetrahydro-2H-pyran-4-yl)methyl)acetamide

Example 71

2-(4-(7-chlorodibenzo[b,d]thiophen-2-yl)phenoxy)-N-((tetrahydro-2H-pyran-4-yl)methyl)acetamide

DEMONSTRATION OF IN VITRO POTENCY OF COMPOUNDS

The PCSK9-LDLR in vitro binding Assay is a quantitative solid phase binding assay between PCSK9 and recombinant LDLR. Plates were pre-coated with a recombinant LDLR-AB domain, which binds PCSK9. Test compound at different concentration was added to the PCSK9 and added to LDLR immobilized on the wells. The amount of bound PCSK9 is measured by binding it with biotinylated anti-His-tag monoclonal antibody, followed by binding with horseradish peroxidase conjugated streptavidin substrate. The color was quantified by ELISA reader at 450 nM which reflects the relative amount of PCSK9 that binds to LDLR in presence and absence of the inhibitor. $EC_{50}$ values were calculated by nonlinear regression analysis using graph pad prism software. Each concentration point represents values in duplicates.

| Example No. | Concentration (μM) | % Inhibition PCSK 9 |
|---|---|---|
| 1 | 10 | 42 |
|   | 100 | 68 |
| 2 | 10 | 9 |
|   | 100 | 33 |
| 3 | 1 | 33 |
|   | 10 | 35 |
|   | 100 | 65 |
| 4 | 10 | 36 |
|   | 100 | 29 |
| 5 | 1 | 49 |
|   | 10 | 67 |
|   | 100 | 71 |
| 6 | 1 | 12 |
|   | 10 | 17 |
|   | 100 | 34 |
| 7 | 1 | 22 |
|   | 10 | 22 |
|   | 100 | 55 |
| 8 | 10 | 73 |
|   | 100 | 58 |
| 9 | 1 | 37 |
|   | 10 | 41 |
|   | 100 | 64 |
| 10 | 1 | 33 |
|   | 10 | 40 |
|   | 100 | 56 |
| 11 | 1 | 30 |
|   | 10 | 44 |
|   | 100 | 53 |
| 12 | 10 | 33 |
|   | 100 | 36 |
| 13 | 1 | 17 |
|   | 10 | 30 |
|   | 100 | 78 |
| 17 | 1 | 40 |
|   | 10 | 38 |
|   | 100 | 63 |
| 18 | 10 | 53 |
| 19 | 10 | 24 |
|   | 100 | 50 |
| 22 | 1 | 27 |
|   | 10 | 30 |
|   | 100 | 54 |
| 24 | 1 | 49 |
|   | 10 | 76 |
|   | 100 | 35 |
| 25 | 1 | 37 |
|   | 10 | 50 |
|   | 100 | 64 |
| 30 | 1 | 19 |
|   | 10 | 20 |
|   | 100 | 32 |
| 31 | 1 | 25 |
|   | 10 | 34 |
|   | 100 | 36 |
| 32 | 1 | 13 |
|   | 10 | 23 |
|   | 100 | 30 |
| 35 | 1 | 14 |
|   | 10 | 54 |
|   | 100 | 61 |
| 36 | 1 | 47 |
|   | 10 | 24 |
|   | 100 | 61 |
| 37 | 1 | 25 |
|   | 10 | 58 |
|   | 100 | 78 |
| 38 | 1 | 27 |
|   | 10 | 39 |
|   | 100 | 59 |
| 39 | 10 | 9.0 |
|   | 100 | 15 |

The compounds of the present invention are suitable for the treatment and/or mitigation of obesity, hyperlipidaemia, hypercholesteremia, hypertension, atherosclerotic disease events, vascular restenosis, diabetes and many other related conditions in humans and animals. The pharmaceutical compositions containing the compounds of the present invention optionally with another suitable pharmaceutical agent can comprise of one or more pharmaceutically acceptable excipients as is known in the art. The formulation can be prepared by suitable techniques well known. The formulation may be in the form of a tablet, capsule, caplet, satchel etc. which are well known to a skilled person. The doses may vary depending on the disease, gravity of the disease, risk profile of the user etc.

We claim:
1. Compounds of formula (I) their tautomeric forms, their stereoisomers, their pharmaceutically acceptable salts, and pharmaceutical compositions containing them wherein

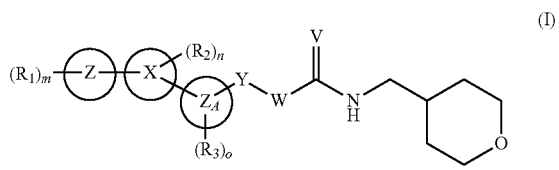

'$Z_A$' represents an optionally substituted ($C_6$)aryl group; each of 'X' and 'Z' independently represents an optionally substituted group selected from ($C_6$)aryl, ($C_2$-$C_5$) heterocyclyl containing one or more heteroatoms selected from O, N, and S or ($C_3$-$C_6$)cycloalkyl groups; $R_1$, $R_2$ and $R_3$ independently at each occurrence represents H, ($C_1$-$C_6$) linear or branched alkyl, ($C_2$-$C_6$) linear or branched alkenyl, ($C_2$-$C_6$) linear or branched alkynyl, hydroxy, ($C_1$-$C_6$) alkoxy, ($C_2$-$C_6$) alkenoxy, hydroxy ($C_1$-$C_6$)alkyl, ($C_1$-$C_6$)alkoxy($C_1$-$C_6$)alkyl, halo($C_1$-$C_6$) alkyl, ($C_3$-$C_6$)cycloalkyl, thio($C_1$-$C_6$)alkyl, ($C_1$-$C_6$) alkylthio, halo, oxo, imino, nitro, ($C_6$)aryl, amino, amino($C_1$-$C_6$)alkyl, cyano, formyl, halo ($C_1$-$C_6$)alkoxy, ($C_6$)aryloxy, ($C_6$)ar($C_1$-$C_6$)alkyl, ($C_6$)ar($C_1$-$C_6$)alkoxy, carboxylic acid, —COOCH$_3$, —COOCH$_2$CH$_3$, —CONH$_2$, ($C_1$-$C_6$)alkylsulfonyl, ($C_1$-$C_6$)alkylsulfonylamino, ($C_1$-$C_6$)alkylsulfonyloxy, each of which may be optionally substituted; 'm''n' and 'o' independently represents integers from 0 to 3; 'Y' represents O; 'W' represents ($C_1$-$C_6$) alkyl; 'V' represents O or S.

2. The compounds as claimed in claim 1 wherein 'X' is selected from optionally substituted ($C_6$)aryl or ($C_2$-$C_5$)heterocyclyl groups.

3. The compounds as claimed in claim 2 wherein the ($C_6$) aryl group is an optionally substituted phenyl group.

4. The compounds as claimed in claim 1 wherein when 'X' represents a ($C_2$-$C_5$)heterocyclyl group, the ($C_2$-$C_5$)heterocyclyl group is selected from mono cyclic aromatic or non-aromatic groups containing one or more hetero atoms selected from O, N or S.

5. The compounds as claimed in claim 3 wherein the ($C_2$-$C_5$)heterocyclyl group is selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, pyrimidinyl, pyrazolyl, pyridazinyl, triazinyl, thiazepinyl, oxazolidinyl, thiazolidinyl, dihydrothiophene, dihydropyran, dihydrofuran, dihydrothiazole, pyrimidonyl, groups.

6. The compounds as claimed in claim 1 wherein 'Z' is ($C_6$)aryl or ($C_2$-$C_5$)heterocyclyl.

7. The compounds as claimed in claim 6 wherein when 'Z' represents ($C_6$)aryl group, the ($C_6$)aryl group is a substituted or unsubstituted phenyl group.

8. The compounds as claimed in claim 6 wherein when 'Z' represents a ($C_2$-$C_5$)heterocyclyl group, the ($C_2$-$C_5$)heterocyclyl group is selected from mono cyclic aromatic or non-aromatic groups containing one or more hetero atoms selected from O, N or S.

9. The compounds as claimed in claim 8 wherein, when 'Z' represents a ($C_2$-05)heterocyclyl group, the ($C_2$-$C_5$)heterocyclyl group is selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, pyrimidinyl, pyrazolyl, pyridazinyl, triazinyl, groups.

10. The compounds as claimed in claim 1 wherein when any of $R_1$, $R_2$ or $R_3$ are substituted, such substituents are selected from hydrogen, hydroxyl, oxo, halo, thiol, nitro, amino, cyano, formyl, or substituted or unsubstituted groups selected from amidino, ($C_1$-$C_3$)alkyl, halo($C_1$-$C_3$)alkyl, perhalo($C_1$-$C_3$)alkyl, ($C_1$-$C_3$)alkoxy, halo($C_1$-$C_3$)alkoxy, and perhalo($C_1$-$C_3$)alkoxy.

11. The compounds of claim 1 selected from
2-(4-(4-methyl-5-phenylisoxazol-3-yl)phenoxy)-N-((tetrahydro-2H-pyran-4-yl)methyl)acetamide;
2-(4-(5-methyl-4-phenylisoxazol-3-yl)phenoxy)-N-((tetrahydro-2H-pyran-4-yl)methyl)acetamide;
2-(4-(5-(4-fluorophenyl)-4-methylisoxazol-3-yl)phenoxy)-N-((tetrahydro-2H-pyran-4-yl)methyl)acetamide;
2-(4-(5-(4-chlorophenyl)-4-methylisoxazol-3-yl)phenoxy)-N-((tetrahydro-2H-pyran-4-yl)methyl)acetamide;
2-(4-(4-methyl-5-(4-(trifluoromethyl)phenyl)isoxazol-3-yl)phenoxy)-N-((tetrahydro-2H-pyran-4-yl)methyl)acetamide;
2-(4-(4-methyl-5-(p-tolyl)isoxazol-3-yl)phenoxy)-N-((tetrahydro-2H-pyran-4-yl)methyl)acetamide;
2-(4-(4-methyl-5-phenylisothiazol-3-yl)phenoxy)-N-((tetrahydro-2H-pyran-4-yl)methyl)acetamide;
2-(4-(5-methoxy-1-(4-(trifluoromethyl)phenyl)-1H-pyrazol-3-yl)phenoxy)-N-((tetrahydro-2H-pyran-4-yl)methyl)acetamide;
2-(4-(1-(4-fluorophenyl)-5-methoxy-1H-pyrazol-3-yl)phenoxy)-N-((tetrahydro-2H-pyran-4-yl)methyl)acetamide;
2-(4-(5-methoxy-1-phenyl-1H-pyrazol-3-yl)phenoxy)-N-((tetrahydro-2H-pyran-4-yl)methyl)acetamide;
2-(4-(4-methyl-2-phenylthiazol-5-yl)phenoxy)-N-((tetrahydro-2H-pyran-4-yl)methyl)acetamide;
2-(4-(4-methyl-2-(4-(trifluoromethyl)phenyl)thiazol-5-yl)phenoxy)-N-((tetrahydro-2H-pyran-4-yl)methyl)acetamide;
2-(4-(2-(4-fluorophenyl)-4-methylthiazol-5-yl)phenoxy)-N-((tetrahydro-2H-pyran-4-yl)methyl)acetamide;
2-(4-(2-(4-bromophenyl)-4-methylthiazol-5-yl)phenoxy)-N-((tetrahydro-2H-pyran-4-yl)methyl)acetamide;
2-(4-(2-(4-chlorophenyl)-4-methylthiazol-5-yl)phenoxy)-N-((tetrahydro-2H-pyran-4-yl)methyl)acetamide;
2-(4-(4-methyl-2-(p-tolyl)thiazol-5-yl)phenoxy)-N-((tetrahydro-2H-pyran-4-yl)methyl)acetamide;
2-(4-(5-methyl-2-phenyloxazol-4-yl)phenoxy)-N-((tetrahydro-2H-pyran-4-yl)methyl)acetamide;
2-(4-(5-methyl-2-(4-(trifluoromethyl)phenyl)oxazol-4-yl)phenoxy)-N-((tetrahydro-2H-pyran-4-yl)methyl)acetamide;
2-(4-(2-(4-fluorophenyl)-5-methyloxazol-4-yl)phenoxy)-N-((tetrahydro-2H-pyran-4-yl)methyl)acetamide;
2-(4-(2-(4-bromophenyl)-5-methyloxazol-4-yl)phenoxy)-N-((tetrahydro-2H-pyran-4-yl)methyl)acetamide;

2-(4-(2-(4-chlorophenyl)-5-methyloxazol-4-yl)phenoxy)-N-((tetrahydro-2H-pyran-4-yl)methyl)acetamide;

2-(4-(5-methyl-2-(p-tolyl)oxazol-4-yl)phenoxy)-N-((tetrahydro-2H-pyran-4-yl)methyl)acetamide;

2-(4-(2-(4-methoxyphenyl)-5-methyloxazol-4-yl)phenoxy)-N-((tetrahydro-2H-pyran-4-yl)methyl)acetamide;

2-(4-(5-methyl-2-(pyridin-3-yl)oxazol-4-yl)phenoxy)-N-((tetrahydro-2H-pyran-4-yl)methyl)acetamide;

N-((tetrahydro-2H-pyran-4-yl)methyl)-2-(4-(5-(4-(trifluoromethyl)phenyl)-1,2,4-oxadiazol-3-yl)phenoxy)acetamide;

2-(4-(5-(4-fluorophenyl)-1,2,4-oxadiazol-3-yl)phenoxy)-N-((tetrahydro-2H-pyran-4-yl)methyl)acetamide;

2-(4-(5-(4-bromophenyl)-1,2,4-oxadiazol-3-yl)phenoxy)-N-((tetrahydro-2H-pyran-4-yl)methyl)acetamide;

2-(4-(5-(4-chlorophenyl)-1,2,4-oxadiazol-3-yl)phenoxy)-N-((tetrahydro-2H-pyran-4-yl)methyl)acetamide;

N-((tetrahydro-2H-pyran-4-yl)methyl)-2-(4-(5-(p-tolyl)-1,2,4-oxadiazol-3-yl)phenoxy)acetamide;

2-(4-(5-(4-fluorophenyl)-1,3,4-oxadiazol-2-yl)phenoxy)-N-((tetrahydro-2H-pyran-4-yl)methyl)acetamide;

N-((tetrahydro-2H-pyran-4-yl)methyl)-2-(4-(5-(4-(trifluoromethyl)phenyl)-1,3,4-oxadiazol-2-yl)phenoxy)acetamide;

2-(4-(5-(4-methoxyphenyl)-1,3,4-oxadiazol-2-yl)phenoxy)-N-((tetrahydro-2H-pyran-4-yl)methyl)acetamide;

2-(4-(5-(4-chlorophenyl)-1,3,4-oxadiazol-2-yl)phenoxy)-N-((tetrahydro-2H-pyran-4-yl)methyl)acetamide;

2-(4-(5-phenyl-1,3,4-oxadiazol-2-yl)phenoxy)-N-((tetrahydro-2H-pyran-4-yl)methyl)acetamide;

2-(4-(3-(4-fluorophenyl)-2-oxooxazolidin-5-yl)phenoxy)-N-((tetrahydro-2H-pyran-4-yl)methyl)acetamide;

2-(4-(3-(4-methoxyphenyl)-2-oxooxazolidin-5-yl)phenoxy)-N-((tetrahydro-2H-pyran-4-yl)methyl)acetamide;

2-(4-(4-phenyl-1H-1,2,3-triazol-1-yl)phenoxy)-N-((tetrahydro-2H-pyran-4-yl)methyl)acetamide;

2-(4-(5-(4-bromophenyl)-4-methylisoxazol-3-yl)phenoxy)-N-((tetrahydro-2H-pyran-4-yl)methyl)acetamide;

2-(4-(5-(4-methoxyphenyl)-4-methylisoxazol-3-yl)phenoxy)-N-((tetrahydro-2H-pyran-4-yl)methyl)acetamide;

2-(4-(4-methyl-5-(4-(trifluoromethoxy)phenyl)isoxazol-3-yl)phenoxy)-N-((tetrahydro-2H-pyran-4-yl)methyl)acetamide;

2-(4-(5-(4-fluorophenyl)-4-methylisothiazol-3-yl)phenoxy)-N-((tetrahydro-2H-pyran-4-yl)methyl)acetamide;

2-(4-(5-(4-chlorophenyl)-4-methylisothiazol-3-yl)phenoxy)-N-((tetrahydro-2H-pyran-4-yl)methyl)acetamide;

2-(4-(5-(4-bromophenyl)-4-methylisothiazol-3-yl)phenoxy)-N-((tetrahydro-2H-pyran-4-yl)methyl)acetamide;

2-(4-(4-methyl-5-(p-tolyl)isothiazol-3-yl)phenoxy)-N-((tetrahydro-2H-pyran-4-yl)methyl)acetamide;

2-(4-(4-methyl-5-(4-(trifluoromethyl)phenyl)isothiazol-3-yl)phenoxy)-N-((tetrahydro-2H-pyran-4-yl)methyl)acetamide;

2-(4-(5-(4-methoxyphenyl)-4-methylisothiazol-3-yl)phenoxy)-N-((tetrahydro-2H-pyran-4-yl)methyl)acetamide;

2-(4-(4-methyl-5-(4-(trifluoromethoxy)phenyl)isothiazol-3-yl)phenoxy)-N-((tetrahydro-2H-pyran-4-yl)methyl)acetamide;

2-(4-(1-(4-chlorophenyl)-5-methoxy-1H-pyrazol-3-yl)phenoxy)-N-((tetrahydro-2H-pyran-4-yl)methyl)acetamide;

2-(4-(5-methoxy-1-(4-methoxyphenyl)-1H-pyrazol-3-yl)phenoxy)-N-((tetrahydro-2H-pyran-4-yl)methyl)acetamide;

2-(4-(5-methoxy-1-(4-(trifluoromethoxy)phenyl)-1H-pyrazol-3-yl)phenoxy)-N-((tetrahydro-2H-pyran-4-yl)methyl)acetamide;

2-(4-(1-(4-bromophenyl)-5-methoxy-1H-pyrazol-3-yl)phenoxy)-N-((tetrahydro-2H-pyran-4-yl)methyl)acetamide;

2-(4-(5-methoxy-1-(p-tolyl)-1H-pyrazol-3-yl)phenoxy)-N-((tetrahydro-2H-pyran-4-yl)methyl)acetamide;

2-(4-(3-(4-chlorophenyl)-2-oxooxazolidin-5-yl)phenoxy)-N-((tetrahydro-2H-pyran-4-yl)methyl)acetamide;

2-(4-(2-oxo-3-(4-(trifluoromethyl)phenyl)oxazolidin-5-yl)phenoxy)-N-((tetrahydro-2H-pyran-4-yl)methyl)acetamide;

2-(4-(2-oxo-3-(4-(trifluoromethoxy)phenyl)oxazolidin-5-yl)phenoxy)-N-((tetrahydro-2H-pyran-4-yl)methyl)acetamide;

2-(4-(3-(4-bromophenyl)-2-oxooxazolidin-5-yl)phenoxy)-N-((tetrahydro-2H-pyran-4-yl)methyl)acetamide;

2-(4-(2-oxo-3-(p-tolyl)oxazolidin-5-yl)phenoxy)-N-((tetrahydro-2H-pyran-4-yl)methyl)acetamide;

2-(4-(4-(4-chlorophenyl)-1H-1,2,3-triazol-1-yl)phenoxy)-N-((tetrahydro-2H-pyran-4-yl)methyl)acetamide;

N-((tetrahydro-2H-pyran-4-yl)methyl)-2-(4-(4-(4-(trifluoromethyl)phenyl)-1H-1,2,3-triazol-1-yl)phenoxy)acetamide;

N-((tetrahydro-2H-pyran-4-yl)methyl)-2-(4-(4-(4-(trifluoromethoxy)phenyl)-1H-1,2,3-triazol-1-yl)phenoxy)acetamide;

2-(4-(4-(4-bromophenyl)-1H-1,2,3-triazol-1-yl)phenoxy)-N-((tetrahydro-2H-pyran-4-yl)methyl)acetamide;

N-((tetrahydro-2H-pyran-4-yl)methyl)-2-(4-(4-(p-tolyl)-1H-1,2,3-triazol-1-yl)phenoxy)acetamide;

2-(4-(4-(4-fluorophenyl)-1H-1,2,3-triazol-1-yl)phenoxy)-N-((tetrahydro-2H-pyran-4-yl)methyl)acetamide;

2-(4-(4-(4-methoxyphenyl)-1H-1,2,3-triazol-1-yl)phenoxy)-N-((tetrahydro-2H-pyran-4-yl)methyl)acetamide;

2-(4-(3-(4-chlorophenyl)-2-iminooxazolidin-5-yl)phenoxy)-N-((tetrahydro-2H-pyran-4-yl)methyl)acetamide;

2-(4-(6-(4-chlorophenyl)pyridin-2-yl)phenoxy)-N-((tetrahydro-2H-pyran-4-yl)methyl)acetamide;

2-(4-(4-(4-chlorophenyl)pyrimidin-2-yl)phenoxy)-N-((tetrahydro-2H-pyran-4-yl)methyl)acetamide.

12. A method for treating hyperlipidemia or dyslipidemia comprising administering one or more compounds of formula (I) as claimed in claim 1 or their pharmaceutical compositions to a subject in need thereof.

13. A pharmaceutical composition comprising compounds of formula (I) as claimed in claim 1, or pharmaceutically acceptable salts thereof, in combination with one or more pharmaceutically active agents selected from the group consisting of insulin, insulin derivatives and mimetics, insulin secretagogues, insulin sensitizers, biguanide agents, alpha-glucosidase inhibitors, insulinotropic sulfonylurea receptor ligands, meglitinides, GLP-1 (glucagon like peptide-1), GLP-1 analogs, DPPIV (dipeptidyl peptidase IV) inhibitors, GPR-119 activators, sodium-dependent glucose co-transporter (SGLT2) inhibitors, PPAR modulators, non-glitazone type PPAR delta agonist, HMG-CoA reductase inhibitors, cholesterol-lowering drugs, rennin inhibitors, anti-thrombotic and anti-platelet agents and anti-obesity agents.

14. A method for treating hyperlipidemia or dyslipidemia comprising administering of the pharmaceutical composition as claimed in claim 13 to a subject in need thereof.

* * * * *